(12) United States Patent
Mrksich et al.

(10) Patent No.: US 10,563,244 B2
(45) Date of Patent: Feb. 18, 2020

(54) NANOPATTERNED EXTRACELLULAR MATRICES ENABLE CELL-BASED ASSAYS WITH A MASS SPECTROMETRIC READOUT

(71) Applicant: NORTHWESTERN UNIVERSITY, Evanston, IL (US)

(72) Inventors: Milan Mrksich, Hinsdale, IL (US); Maria D. Cebezas, Evanston, IL (US); Chad A. Mirkin, Wilmette, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 321 days.

(21) Appl. No.: 15/710,475

(22) Filed: Sep. 20, 2017

(65) Prior Publication Data
US 2018/0080058 A1 Mar. 22, 2018

Related U.S. Application Data

(60) Provisional application No. 62/396,972, filed on Sep. 20, 2016.

(51) Int. Cl.
*C12Q 1/42* (2006.01)
*C12Q 1/37* (2006.01)
*C12Q 1/34* (2006.01)

(52) U.S. Cl.
CPC .......... *C12Q 1/42* (2013.01); *C12Q 1/34* (2013.01); *C12Q 1/37* (2013.01); *C12Y 304/22044* (2013.01); *C12Y 305/01098* (2013.01); *G01N 2333/916* (2013.01); *G01N 2333/95* (2013.01); *G01N 2333/98* (2013.01); *G01N 2560/00* (2013.01); *G01N 2610/00* (2013.01)

(58) Field of Classification Search
None
See application file for complete search history.

(56) References Cited

U.S. PATENT DOCUMENTS

| | | | |
|---|---|---|---|
| 5,472,881 A | 12/1995 | Beebe et al. | |
| 5,776,748 A | 7/1998 | Singhvi et al. | |
| 5,846,909 A | 12/1998 | McDevitt et al. | |
| 5,908,692 A | 6/1999 | Hamers et al. | |
| 5,942,397 A | 8/1999 | Tarlov et al. | |
| 6,500,549 B1 | 12/2002 | Deppisch et al. | |
| 6,596,346 B2 | 7/2003 | Bernard et al. | |
| 2004/0228962 A1 | 11/2004 | Liu et al. | |
| 2010/0112722 A1 | 5/2010 | Mrksich et al. | |

FOREIGN PATENT DOCUMENTS

| WO | WO-1999/48682 A1 | 9/1999 |
|---|---|---|
| WO | WO-2009/132321 A1 | 10/2009 |

OTHER PUBLICATIONS

Allara et al., "Spontaneously Organized Molecular Assemblies. 1. Formation, Dynamics, and Physical Properties of n-Alkanoic Acids Adsorbed from Solution on an Oxidized Aluminum Surface," Langmuir, 1:45-52 (1985).
Anwander et al., "Surface Characterization and Functionalization of MCM-41 Silicas via Silazane Silylation," J. Phys. Chem. B, 104:3532-3244 (2000).
Arabaci et al., "α-Haloacetophenone Derovatoves as photoreversible Covalent lnhibotrs of Protein Tyrosine Phosphatases," J. Am. Chem. Soc. 121, (21), 5085-5086 (1999).
Bain, "A New Class of Self-Assembled Monolayers: Organic Thiols on Gallium Arsenide," Adv. Mater. 4(9):591-594 (1992).
Ban et al., "Discovery of Glycosyltransferases Using Carbohydrate Arrays and Mass Spectrometry," Nat Chem Biol 8(9):769-773 (2012).
Ban et al., "On-Chip Synthesis and Label-Free Assays of Oligosaccharide Arrays," Angew Chem Int Ed Eng 47:3396-3399 (2008).
Bansal et al., "Electrochemical Properties of (111)-Oriented n-Si Surfaces Derivatized with Covalently-Attached Alkyl Chains," J. Phys. Chem. B, 102(7):1067-1070 (1998).
Bansal et al., "Stabilization of Si Photoanodes in Aqueous Electrolytes through Surface Alkylation," J. Phys. Chem. B. 102:4058-4060 (1998).
Bernard et al., "Printing Patterns of Proteins," Langmuir, 14(9):2225-2229 (1998).
Berns et al., "Cellular Assays with a Molecular Endpoint Measured by SAMDI Mass Spectrometry," Small 12(28):3811-3818 (2016).
Bishop et al., "Self-assembled monolayers: recent developments and applications," Curr. Opinion Colloid & Interface Sci., 1:127-136 (1996).
Braunschweig et al., "Molecular Printing," Nat. Chem. 1:353-358 (2009).
Brazdil et al., "Resonance Raman Spectra of Adsorbed Species at Solid-Gas Interfaces. 2. p-Nitrosodimethylaniline and p-Dimethylaminoazobenzene Adsorbed on Semiconductor Oxide Surfaces," J. Phys. Chem., 85:1005-1014 (1981).
Burwell, "Modified silica gels as adsorbents and catalysts," Chemical Technology, 4:370-377 (1974).
Cabrera-Pardo, et al., "Label-Assisted Mass Spectrometry for the Acceleration of Reaction Discovery and Optimization," Nat. Chem. 5(5):423-427 (2013).
Cai et al., "Enzymatic Synthesis and Properties of Uridine-5'-O-(2-thiodiphospho)-N-acetylglucosamine," Carbohydr Res 346(12):1576-1580 (2011).
Calvert, "Lithographic patterning of self-assembled films," J. Vac. Sci. Technol. B, 11(5):2155-2163 (1993).
Chang et al., "Structures of Self-Assembled Monolayers of Aromatic-Derivatized Thiols on Evaporated Gold and Silver Surfaces: Implication on Packing Mechanism," J. Am. Chem. Soc., 116:6792-6805 (1994).

(Continued)

*Primary Examiner* — Christopher M Gross
(74) *Attorney, Agent, or Firm* — Marshall, Gerstein & Borun LLP

(57) ABSTRACT

The present disclosure provides methods in which adherent cells are treated with small molecules, cultured, lysed, and then analyzed by mass spectrometry to measure the activities of endogenous enzymes. The implementation of this method relies on the use of surfaces that are nanopatterned with cell adhesion ligands to mediate cell attachment and a peptide that is a substrate for the desired enzyme activity in the lysate.

20 Claims, 8 Drawing Sheets

Specification includes a Sequence Listing.

(56) References Cited

OTHER PUBLICATIONS

Chen et al., "Do Alkanethoils Adsorb onto the Surfaces of Tl—Ba—Ca—Cu—O-Based High-Temperature Superconductors? The Critical Role of $H_2O$ Content on the Adsorption Process," Langmuir, 12:2622-2624 (1996).
Chen et al., "Surveying the Surface Coordination Chemistry of a Superconductor: Spontaneous Adsorption of Monolayer Films of Redox-Active "Ligands" on $YBa_2Cu_{3O7-\delta}$," J. Am. Chem. Soc., 117:6374-6375 (1995).
Chen et al., "Synthesis and Characterization of Carboxylate-Modified Gold Nanoparticle Powders Dispersible in Water," Langmuir, 15:1075-1082 (1999).
Chidsey, Book of Abstracts, 214th ACS National Meeting, Las Vegas, Nev., Sep. 7-11, 1997, I&EC-027.
Dammel, Diazonaphthoquinone-based resists (1st ed., SPIE Optical Engineering Press, Bellingham, Wash. (1993).
Dillmore et al., "A Photochemical Method for Patterning the Immobilization of Ligands and Cells to Self-Assembled Monolayers," Langmuir 20: 7223-7231 (2004).
Donzel et al., "Hydrophilic Poly (dimethylsiloxane) Stamps for Microcontact Printing," Adv. Mater. 13(15):1164-1167 (2001).
Dubois et al., "Synthesis, Structure, and Properties of Model Organic Surfaces," Annu. Rev. Phys. Chem., 43:437-463 (1992).
Eichelsdoerfer et al., "Large-area molecular patterning with polymer pen lithography," Nat. Protoc. 8(12):2548-2560 (2013).
Ellison et al., "Adsorption of Phenyl Isothiocyanate on Si(001): A 1,2-Dipolar Surface Addition Reaction," J. Phys. Chem. B, 103:6243-6251 (1999).
Ellison et al., "Cycloaddition Chemistry on Silicon(001) Surfaces: The Adsorption of Azo-tert-butane," J. Phys. Chem. B, 102:8510-8518 (1998).
Eltekova et al., "Adsorption of Aromatic Compounds from Solutions on Titanium Dioxide and Silica," Langmuir, 3:951-957 (1987).
Feng et al., "The Synergy Peptide PHSRN and the Adhesion Peptide RGD Mediate Cell Adhesion through a Common Mechanism," Biochemistry 43:15811-15821 (2004).
Fenter et al., "Structure of $CH_3(CH_2)_{17}SH$ Self-Assembled on the Ag(111) Surface: An Incommensurate Monolayer," Langmuir, 7:2013-2016 (1991).
Frantz et al., "The extracellular matrix at a glance," J. Cell Sci. 123(24):4195-4200 (2010).
Gawalt et al., "A Substituent Effects Study Reveals the Kinetic Pathway for an Interfacial Reaction," J Am Chem Soc 126:15613-7 (2004).
Giam et al., "Cantilever-Free Scanning Probe Molecular Printing**," Angew. Chem., Int. Ed. 2011, 50:7482-7485 (2011).
Giam et al., "Scanning probe-enabled nanocombinatorics define the relationship between fibronectin feature size and stem cell fate," Proc. Natl. Acad. Sci. U.S.A. 109(12):4377-4382 (2012).
Ginger et al., "The Evolution of Dip-Pen Nanolithography," Angew. Chem., Int. Ed, 43(1):30-45 (2004).
Grabar et al., "Preparation and Characterization of Au Colloid Monolayers," Anal. Chem., 67:735-743 (1995).
Gu et al., "Electron Tunneling at the Semiconductor—Insulator—Electrolyte Interface. Photocurrent Studies on the n-InP-Alkanethiol-Ferrocyanide System," J. Phys. Chem. B, 102:9015-9028 (1998).
Gui et al., "Adsorption and Surface Structural Chemistry of Thiophenol, Benzyl Mercaptan, and Alkyl Mercaptans. Comparative Studies at Ag(111) and Pt(111) Electrodes by Means of Auger Spectroscopy, Electron Diffraction, and Electrochemistry," Langmuir, 7:955-963 (1991).
Gurard-Levin et al., "Combining Mass Spectrometry and Peptide Arrays to Profile the Specificities of Histone Deacetylases," Chembiochem 10:2159-2161 (2009).
Gurard-Levin et al., "Combining Self-Assembled Monolayers and Mass Spectrometry for Applications in Biochips," Annu Rev Anal Chem 1:767-800 (2008).
Gurard-Levin et al., "High-Throughput Screening of Small Molecule Libraries using SAMDI Mass Spectrometry," ACS Comb Sci 13:347-350 (2011).
Gurard-Levin et al., "Peptide Arrays Identify Isoform-Selective Substrates for Profiling Endogenous Lysine Deacetylase Activity," ACS Chem Biol 5(9):863-873 (2010).
Gurard-Levin et al., "The Activity of HDAC8 Depends on Local and Distal Sequences of Its Peptide Substrates," Biochemistry 47:6242-6250 (2008).
Hamers et al., "Formation of Ordered, Anisotropic Organic Monolayers on the Si(001) Surface," J. Phys. Chem. B, 101:1489-1492 (1997).
He et al., "Preparation of Hydrophilic Poly(dimethylsiloxane) Stamps by Plasma-Induced Grafting," Langmuir 19:6982-6986 (2003).
Henderson et al., "Self-assembled monolayers of dithiols, diisocyanides, and isocyanothils on gold: 'chemically sticky' surfaces for covalent attachment of metal clusters and studies of interfacial electron transfer," Inorg. Chim. Acta, 242:115-24 (1996).
Hickman et al., "Combining Spontaneous Molecular Assembly with Microfabrication to Pattern Surfaces: Selective Binding of Isonitriles to Platinum Microwires and Characterization by Electrochemistry and Surface Spectroscopy," J. Am. Chem. Soc., 111:7271-7272 (1989).
Hickman et al., "Toward Orthogonal Self-Assembly of Redox Active Molecules on Pt and Au: Selective Reaction of Disulfide with Au and Isocyanide with Pt," Langmuir, 8:357-359 (1992).
Hodneland et al., "Design of Self-Assembled Monolayers That Release Attached Groups Using Applied Electrical Potentials," Langmuir 13: 6001-6003 (1997).
Hodneland et al., "Selective immobilization of proteins to self-assembled monolayers presenting active site-directed capture ligands," Proc Natl Acad Sci USA 99: 5048-5052 (2002).
Houseman et al., "Carbohydrate Arrays for the Evaluation of Protein Binding and Enzymatic Modification," Chem Biol 9: 443-454 (2002).
Houseman et al., "Environment of Arg-Gly-Asp ligands influences the adhesion of fibroblasts to self-assembled monolayers," Cell Attachment to the Extracellular Matrix, p. 430a, Abstract 2494 (1998).
Houseman et al., "Maleimide-Functionalized Self-Assembled Monolayers for the Preparation of Peptide and Carbohydrate Biochips," Langmuir 19: 1522-1531 (2003).
Houseman et al., "Model substrates for the dynamic control of cell behavior," Extracellular Matrix Cell Behavior, p. 45a, Abstract 232 (2000).
Houseman et al., "Model Systems for Studying Polyvalent Carbohydrate Binding Interactions," Top Curr Chem 218 1-44 (2002).
Houseman et al., "Peptide chips for the quantitative evaluation of protein kinase activity," Nat Biotechnol 20: 270-274 (2002).
Houseman et al., "The microenvironment of immobilized Arg-Gly-Asp peptides is an important determinant of cell adhesion," Biomaterials 22: 943-955 (2001).
Houseman et al., "The Role of Ligand Density in the Enzymatic Glycoslyation of Carbohydrates Presented on Self-Assembled Monolayers of Alkanethiolates on Gold," Angew Chem Int Ed 38: 782-785 (1999).
Houseman et al., "Towards quantitative assays with peptide chips: a surface engineering approach," Trends Biotechnol 20: 279-281 (2002).
Houseman et al., "Using self-assembled monolayers that present Arg-Gly-Asp peptide ligands to study adhesion of fibroblasts," Extracellular Matrix-Cell Interaction, 11: p. A1095, Abstract 1395 (1997).
Hovis et al., "Cycloaddition chemistry and formation of ordered organic monolayers on silicon (001) surfaces," Surf. Sci., 402-404:1-7 (1998).
Hovis et al., "Cycloaddition Chemistry of 1,3-Dienes on the Silicon(001) Surface: Competition between [4 + 2] and [2 + 2] Reactions," J. Phys. Chem. B, 102:6873-6879 (1998).
Hovis et al., "Structure and Bonding of Ordered Organic Monolayers of 1,5-Cyclooctadiene on the Silicon(001) Surface," J. Phys. Chem. B, 101:9581-9585 (1997).

(56) References Cited

OTHER PUBLICATIONS

Hubbard, "Electrochemistry of Well-Defined Surfaces," Acc. Chem. Res., 13:177-184 (1980).
Huc et al., "Self-Assembled Mono- and Multilayers on Gold from 1,4-Diisocyanobenzene and Ruthenium Phthalocyanine," J. Phys. Chem. B, 103:10489-10495 (1999).
Huo et al., "Polymer Pen Lithography," Science 321:1658-1660 (2008).
Iler, "Solubility, Polymerization, Colloid and Surface Properties, and Biochemistry," The Chemistry of Silica, Chapter 6, (Wiley 1979).
Inglese et al., "High-throughput screening assays for the identification of chemical probes," Nat. Chem. Biol. 3(8):466-479 (2007).
James et al., "Patterned Protein Layers on Solid Substrates by Thin Stamp Microcontact Printing," Langmuir, 14:741-744 (1998).
Maduram et al., "Subcellular curvature at the perimeter of micropatterned cells influences lamellipodial distribution and cell polarity," Cell Motil Cytoskeleton 65 841-852 (2008).
Kato et al., "Rewiring Cell Adhesion," J Am Chem Soc 126: 6504-6505 (2004).
Kato et al., "Using model substrates to study the influence of affinity on cell adhesion," Abstracts, Division of Biological Chemistry, 222nd National Meeting of the American Chemical Society, Aug. 26-29, 2001, Biochemistry 40: 8608-8608 (2001).
Kepp et al., "Cell death assays for drug discovery," Nat. Rev. Drug Discov. 10(3):221-237 (2011).
Kim et al., "Profiling the selectivity of DNA ligases in an array format with mass spectrometry," Nucleic Acids Res 38(1):e2, 10 pages (2010).
Kwon et al., "Dependence of the Rate of an Interfacial Diels—Alder Reaction on the Steric Environment of the Immobilized Dienophile: An Example of Enthalpy-Entropy Compensation," J Am Chem Soc 124: 806-812 (2002).
Laibinis et al., "Comparisons of Self-Assembled Monolayers on Silver and Gold: Mixed Monolayers Derived from $HS(CH_2)_{21}X$ and $HS(CH_2)_{10}Y$ (X, Y—$CH_3$, $CH_2OH$) Have Similar Properties," Langmuir, 7:3167-3173 (1991).
Laibinis et al., "ω-Terminated Alkanethiolate Monolayers on Surfaces of Copper, Silver, and Gold Have Similar Wettabilities," J. Am. Chem. Soc., 114:1990-1995 (1992).
Lee et al., "Adsorption of Ordered Zirconium PHosphonate Multilayer Films on Silicon and Gold Surfaces," J. Phys. Chem., 92:2597-2601 (1988).
Lee et al., "Protein Nanoarrays Generated by Dip-Pen Nanolithography," Science 295:1702-1705 (2002).
Lee et al., "Protein Nanostructures Formed via Direct-Write Dip-Pen Nanolithography," J. Am. Chem. Soc. 125(19):5588-5589 (2003).
Li et al., "Catalytic Asymmetric Dihydroxylation by Gold Colloids Functionalized with Self-Assembled Monolayers," Langmuir 15: 4957-4959 (1999).
Li et al., "Rapid Evaluation and Screening of Interfacial Reactions on Self-Assembled Monolayers," Langmuir 23:11826-11835 (2007).
Li et al., "Self-Assembly of n-Alkanethiolate Monolayers on Silver Nanostructures: Determination of the Apparent Thickness of the Monolayer by Scanning Tunnelling Microscopy," J. Phys. Chem., 98:11751-11755 (1994).
Li et al., "Steady-State of an Enzymatic Reaction is Dependent on the Density of Reactant," Langmuir 29:294-298 (2013).
Li et al., "The Hippocampal CA3 Network: An in Vivo Intracellular Labeling Study," The Journal of Comparative Neurology 339:181-208 (1994).
Liang et al., "In vitro scratch assay: a convenient and inexpensive method for analysis of cell migration in vitro," Nat. Protoc. 2(2):329-333 (2007).
Liao et al., "A Spatially Propagating Biochemical Reaction," Angew Chem Int Ed Engl 50:706-708 (2011).
Liao et al., "An Adaptor Domain-Mediated Auto-Catalytic Interfacial Kinase Reaction," Chemistry 15(14):12303-12309 (2009).
Liao et al., "Force- and Time-Dependent Feature Size and Shape Control in Molecular Printing via Polymer-Pen Lithography**," Small 6(10):1082-6 (2010).
Lim et al., "Direct-Write Dip-Pen Nanolithography of Proteins on Modified Silicon Oxide Surfaces," Angew. Chem., Int. Ed. 42(20):2309-2312 (2003).
Lo et al., "Polypyrrole Growth on YBa2CU3O7-δ Modified with a Self-Assembled Monolayer of n-(3-Aminopropyl)pyrrole: Hardwiring the "Electroactive Hot Spots" on a Superconductor Electrode," J. Am. Chem. Soc., 118:11295-11296 (1996).
Luk et al., "Self-Assembled Monolayers of Alkanethiolates Presenting Mannitol Groups Are Inert to Protein Adsorption and Cell Attachment," Langmuir 16: 9604-9608 (2000).
Luk et al., Stereochemical control of cell adhesion on self-assembled monolayers presenting organized saccharides: Potential effects of template water structure, Abstract 233, p. 8467, Division of Biological Chemistry, 226th National Meetings of the American Chemical Society, Sep. 7-11, 2003. Biochemistry, 42: 8594-8652 (2003).
Lunt et al., "Chemical studies of the passivation of GaAs surface recombination using sulfides and thiols," J. Appl. Phys., 70:7449-7467 (1991).
Lunt et al., "Passivation of GaAs recombination with organic thiols," J. Vac. Sci. Technol., B, 9:2333-2336 (1991).
Magallon et al., "Structural Characterization of N-Alkyl Amine Monolayers on Copper by Ellipsometry and Infrared Spectroscopy," Abstract 048—Book of Abstracts, 215th ACS National Meeting, Dallas, Mar. 29-Apr. 2, 1998.
Mahmoud et al., "Green Fluorescent Protein Reporter System with Transcriptional Sequence Heterogeneity for Monitoring the Interferon Response," J. Virol. 85(18):9268-9275 (2011).
Maoz et al., "Penetration-Controlled Reactions in Organized Monolayer Assemblies. 1. Aqueous Permanganate Interaction with Monolayer and Multilayer Films of Long-Chain Surfactants," Langmuir 3:1034-1044 (1987).
Maoz et al., "Penetration-Controlled Reactions in Organized Monolayer Assemblies. 2. Aqueous Permanganate Interaction with Self-Assembling Monolayers of Long-Chain Surfactants," Langmuir 3:1045-1051 (1987).
Marin et al., "Functional Assays of Membrane-Bound Proteins with SAMDI-TOF Mass Spectrometry," Angew Chem Int Ed Engl 46(46):8796-8798 (2007).
Martin et al., "Direct Protein Microarray Fabrication Using a Hydrogel "Stamper"," Langmuir 14(15):3971-3975 (1998).
Matteucci et al., "Synthesis of Deoxyoligonucleotides on a Polymer Support," J. Am. Chem. Soc., 103:3185-3191 (1981).
Mayya et al., "A Study of the Partitioning of Colloidal Particles Based on Their Size during Electrostatic Immobilization at the Air-Water Interface Using Fatty Amine Monolayers," J. Phys. Chem. B, 101:9790-9793 (1997).
Meli et al., "Three Dimensional Cellular Microarray Platform for Human Neural Stem Cell Differentiation and Toxicology," Stem Cell Res. 13(1):36-47 (2014).
Menzel et al., "Surface-Confined Nanoparticles as Substrates for Photopolymerizable Self-Assembled Monolayers**," Adv. Mater. 11(2):131-134 (1999).
Meyer et al., "Evidence for Adduct Formation at the Semiconductor-Gas Interface. Photoluminescent Properties of Cadmium Selenide in the Presence of Amines," J. Am. Chem. Soc., 110:4914-4918 (1988).
Min et al., "A Method for Connecting Solution-Phase Enzyme Activity Assays with Immobilized Format Analysis by Mass Spectrometry," Anal Chem 76:3923-3929 (2004).
Min et al., "Peptide arrays: towards routine implementation," Curr Opin Chem Biol 8:554-558 (2004).
Min et al., "Profiling Kinase Activities by Using a Peptide Chip and Mass Spectrometry," Angewandte Chemie 43:5973-5977 (2004).
Mirkin et al., "Controlling the Surface Properties of High Temperature Superconductors**," Adv. Mater. 9(2):167-173 (1997).
Montavon et al., "Three-Component Reaction Discovery Enabled by Mass Spectrometry of Self-Assembled Monolayers," Nat Chem 4(1):45-51 (2012).

(56) References Cited

OTHER PUBLICATIONS

Mrksich et al., "Using Self-Assembled Monolayers that Present Oligo(ethylene glycol) Groups to Control the Interactions of Proteins with Surfaces," Acs Sym Ser 680: 361-373 (1997).
Mrksich et al., "Using self-assembled monolayers to model the extracellular matrix," Acta Biomater. 5(3):832-841 (2009).
Mrksich et al., "Using Self-Assembled Monolayers to Understand the Interactions of Man-Made Surfaces with Proteins and Cells," Annu Rev Biophys Biomol Struct 25: 55-78 (1996).
Mrksich, "A surface chemistry approach to studying cell adhesion," Chem Soc Rev 29: 267-273 (2000).
Mrksich, "Dynamic Substrates for Cell Biology," MRS Bull 30:180-184 (2005).
Mrksich, "Mass Spectrometry of Self-Assembled Monolayers: A New Tool for Molecular Surface Science," ACS Nano 2(1):7-18 (2008).
Mrksich, "Tailored substrates for studies of attached cell culture," Cell Mol Life Sci 54: 653-662 (1998).
Mrksich, "Using self-assembled monolayers to understand the biomaterials interface," Curr Opin Colloid in 2: 83-88 (1997).
Mrksich, "What can surface chemistry do for cell biology?", Curr Opin Chem Biol 6: 794-797 (2002).
Mucic et al., "Synthesis and characterization of DNA with ferrocenyl groups attached to their 5'-termini: electrochemical characterization of a redox-active nucleotide monolayer," Chem. Commun. 555-557 (1996).
Murphy et al., "Substrates for Cell Adhesion Prepared Via Active Site-Directed Immobilization of a Protein Domain," Langmuir 20:1026-1030 (2004).
Nakagawa et al., "GaAs Interfaces with Octadecyl Thiol Self-Assembled Monolayer: Structural and Electrical Properties," Jpn. J. Appl. Phys., 30(12B):3759-3762 (1991).
Nuzzo et al., "Spontaneously Organized Molecular Assemblies. 3. Preparation and Properties of Solution Adsorbed Monolayers of Organic Disulfides on Gold Surfaces," J. Am. Chem. Soc., 109:2358-2368 (1987).
Ohno et al., "Nanostructural Formation of Self-Assembled Monolayer Films on Cleaved AlGaAs/GaAs Heterojuctions," Mol. Cryst. Liq. Cryst. 295:189-192/487-490 (1997).
Patel et al., "Discovery of SIRT3 Inhibitors Using SAMDI Mass Spectrometry," J. Biomol. Screen 20(7):842-848 (2015).
Patil et al., "Surface Derivatization of Colloidal Silver Particles Using Interdigitated Bilayers: A Novel Strategy for Electrostatic Immobilization of Colloidal Particles in Thermally Evaporated Fatty Acid/Fatty Amine Films," Langmuir, 14:2707-2711 (1998).
Patrie et al., "Self-Assembled Monolayers for MALDI-TOF Mass Spectrometry for Immunoassays of Human Protein Antigens," Anal Chem 79:5878-5887 (2007).
Pereira et al., "Modification of surface properties of alumina by plasma treatment," J. Mater. Chem., 10:259-261 (2000).
Piner et al., "Dip-Pen Nanolithography," Science 283:661-663 (1999).
Porter et al., "Gold and Silver Nanoparticles Functionalized by the Adsorption of Dialkyl Disulfides," Langmuir, 14:7378-7386 (1998).
Prats-Alfonso et al., "Cancer Prognostics by Direct Detection of p53-Antibodies on Gold Surfaces by Impedance Measurements," Small 8(13):2106-2115 (2012).
Reuter et al., "Effects of Gallium Arsenide Passivation on Scanning Tunneling Microscope Excited Luminescence," Mater. Res. Soc. Symp. Proc., 380:119-124 (1995).
Ruoslahti et al., "RGD and Other Recognition Sequences for Integrins," Annu. Rev. Cell Dev. Biol. 12:697-715 (1996).
Salaita et al., "Applications of dip-pen nanolithography," Nanotechnol. 2:145-155 (2007).
Sangiorgi et al., "Adsorption of 1-Decylamine on Copper," Gazz. Chim. Ital., 111:99-102 (1981).
Sastry et al., "Langmuir-Blodgett Films of Carboxylic Acid Derivatized Silver Colloidal Particles: Role of Subphase pH on Degree of Cluster Incorporation," J. Phys. Chem. B, 101:4954-4958 (1997).
Schmid et al., "Siloxane Polymers for High-Resolution, High-Accuracy Soft Lithography," Macromolecules, 33:3042-3049 (2000).
Sheen et al., A New Class of Organized Self-Assembled Monolayers: Alkane Thiols on GaAs (1000), J. Am. Chem. Soc., 114:1514-1515 (1992).
Slavov et al., "Mechanism of Silation of Silica with Hexamethydisilazane," J. Phys. Chem., 104:983-989 (2000).
Solomun et al., "On the Promoting Effect of Alkali Metals on the Adsorption of Nitriles on the Gold(100) Surface," Ber. Bunsen-Ges. Phys. Chem., 95(1):95-98 (1991).
Solomun et al., "The Interaction of Nitriles with a Potassium-Promoted Gold(100) Surface," J. Phys. Chem., 95:10041-10049 (1991).
Son et al., "Adsorption of 4-Methoxybenzyl Cyanide on Silver and Gold Surfaces Investigated by Fourier Transform Infrared Spectroscopy," J. Phys. Chem., 98:8488-8493 (1994).
Song, "Quenching of Porous Silicon Photoluminescence by Aromatic Molecules, and Surface Derivatization of Porous Silicon with Dimethyl Sulfoxide, Aryllithium, or Alkyllithium Reagents," J. H., Thesis, University of California at San Diego (1998).
Songyang et al., "Catalytic specificity of protein-tyrosine kinases is critical for selective signalling," Nature 373:536-539 (1995).
Songyang et al., "SH2 Domains Recognize Specific Phosphopeptide Sequences," Cell 72(5):767-778 (1993).
Soriaga et al., "Determination of the Orientation of Aromatic Molecules Adsorbed on Platinum Electrodes. The Effect of Solute Concentration," J. Am. Chem. Soc., 104:3937-3945 (1982).
Steiner et al., "Adsorption of Alkanenitriles and Alkanedinitriles on Gold and Copper," Langmuir, 8:2771-2777 (1992).
Steiner et al., "Adsorption of $NPh_3$, $PPh_3$, $AsPh_3$, $SbPh_3$, and $BiPh_3$ on Gold and Copper," Langmuir, 8:90-94 (1992).
Su et al., "Using MALDI-TOF Mass Spectrometry to Characterize Interfacial Reactions on Self-Assembled Monolayers," Langmuir 19(12):4867-4870 (2003).
Su et al., "Using Mass Spectrometry to Characterize Self-Assembled Monolayers Presenting Peptides, Proteins, and Carbohydrates," Angew Chem Int Ed Eng. 41(24):4715-4718 (2002).
Tao, "Structural Comparison of Self-Assembled Monolayers of n-Alkanoic Acids on the Surfaces of Silver, Copper, and Aluminum," J. Am. Chem. Soc., 115:4350-4358 (1993).
Timmons et al., "Investigation of Fatty Acid Monolayers on Metals by Contact," J. Phys. Chem., 69, 984-990 (1965).
Tompkins et al., "The Study of the Gas-Solid Interaction of Acetic Acid with a Cuprous Oxide Surface Using Reflection-Absorption Spectroscopy," J. Colloid Interfate Sci., 49(3):410-421 (1974).
Tsien et al., "The Green Fluorescent Protein," Annu. Rev. Biochem. 67:509-544 (1998).
Tsubery et al., "Biochemical Assays of Immobilized Oligonucleotides with Mass Spectrometry," Langmuir 24:5433-5438 (2008).
Ulman, "Formation and Structure of Self-Assembled Monolayers," Chem. Rev., 96:1533-1554 (1996).
Ulman, An Introduction to Ultrathin Organic Films: From Langmuir-Blodgett to Self-Assembly (Academic, Boston, 1991).
Vega et al., "Monitoring Single-Cell Infectivity from Virus-Particle Nanoarrays Fabricated by Parallel Dip-Pen Nanolithography," Small 3(9):1482-1485 (2007).
Walczak et al., "Structure and Interfacial Properties of Spontaneously Adsorbed n-Alkanethiolate Monolayers on Evaporated Silver Surfaces," J. Am. Chem. Soc., 113:2370-2378 (1991).
Wang et al., "Scanning Probe Contact Printing," Langmuir 19:8951-8955 (2003).
Wasserman et al., "Structure and Reactivity of Alkylsiloxane Monolayers Formed by Reaction of Alkyltrichlorosilanes on Silicon Substrates," Langmuir, 5:1074-1087 (1989).
Whitesides, Proceedings of the Robert A. Welch Foundation 39th Conference on Chemical Research Nanophase Chemistry, Houston, Tex., pp. 109-121 (1995).
Xia et al., "Soft Lithography," Angew. Chem. Int. Ed., 37:550-575 (1998).
Xu et al., "Surface Coordination Chemistry of $YBa_2Cu_3O_{7-\delta}$," Langmuir, 14:6505-6511 (1998).

(56) References Cited

OTHER PUBLICATIONS

Yamamoto et al., "Characterization of the Surface to Thiol Bonding in Self-Assembled Monolayer Films of C12H25SH on Inp(100) by Angle-Resolved X-ray Photoelectron Spectroscopy," Langmuir 15:8640-8644 (1999).

Yeo et al., "Electroactive Monolayer Substrates that Selectively Release Adherent Cells," Chembiochem 2: 590-593 (2001).

Yeo et al., "Electroactive Substrates that Reveal Aldehyde Groups for Bio-Immobilization," Adv Mater 16(15):1352-1356 (2004).

Yeo et al., "Label-Free Detection of Protein-Protein Interactions on Biochips," Angew Chem Int Ed Engl 44:5480-5483 (2005).

Yeo et al., "Self-Assembled Monolayers That Transduce Enzymatic Activities to Electrical Signals," Angew Chem Int Ed Engl 42: 3121-3124 (2003).

Yonezawa et al., "Layered Nanocomposite of Close-Packed Gold Nanoparticles and $TiO_2$ Gel Layers," Chem. Mater., 11:33-35 (1999).

Yonzon et al., "A Comparative Analysis of Localized and Propagating Surface Plasmon Resonance Sensors: The Binding of Concanavalin A to a Monosaccharide Functionalized Self-Assembled Monolayer," J Am Chem Soc 126:12669-12676 (2004).

Yousaf et al., "Diels-Alder Reaction for the Selective Immobilization of Protein to Electroactive Self-Assembled Monolayers," J Am Chem Soc 121: 4286-4287 (1999).

Yousaf et al., "Electroactive substrates that modulate cell growth," Abstract 170, p. 1580, Biochemistry 39(6):1542-1582 (2000).

Yousaf et al., "The Kinetic Order of an Interfacial Diels-Alder Reaction Depends on the Environment of the Immobilized Dienophile," Angew Chem Int Ed Engl 39: 1943-1946 (2000).

Yousaf et al., "Turning on Cell Migration with Electroactive Substrates**," Angew Chem Int Ed Engl 40: 1093-1096 (2001).

Yousaf et al., "Using electroactive substrates to pattern the attachment of two different cell populations," Proc Natl Acad Sci USA 98: 5992-5996 (2001).

Zhang, et al., "Dip Pen Nanolithography Stamp Tip," Nano Lett. 4(9):1649-1655 (2004).

U.S. Appl. No. 15/051,338, Published as US-2016-0252501, filed Feb. 23, 2016.

FIGURE 8
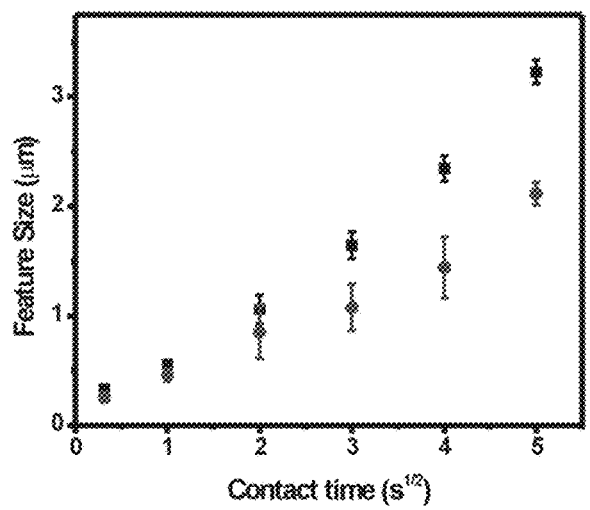
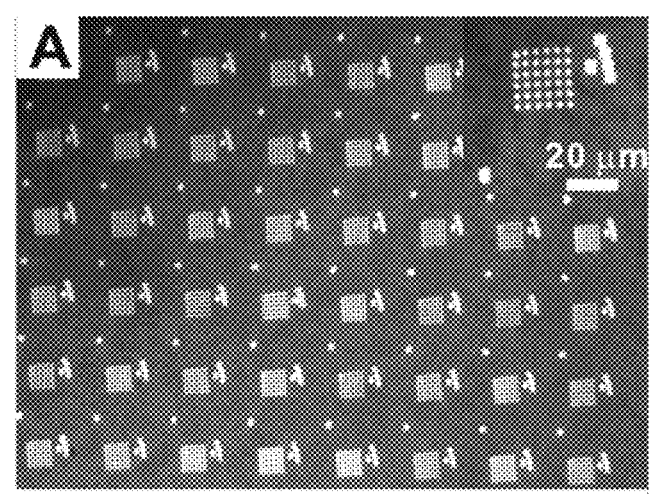
FIGURE 9A
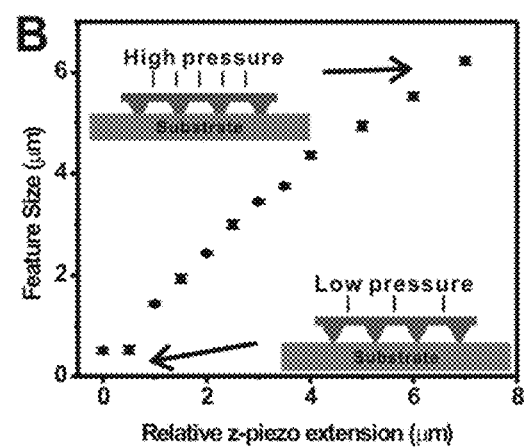
FIGURE 9B
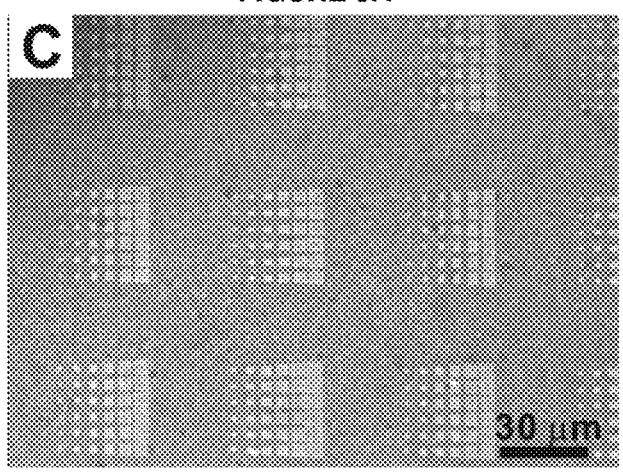
FIGURE 9C
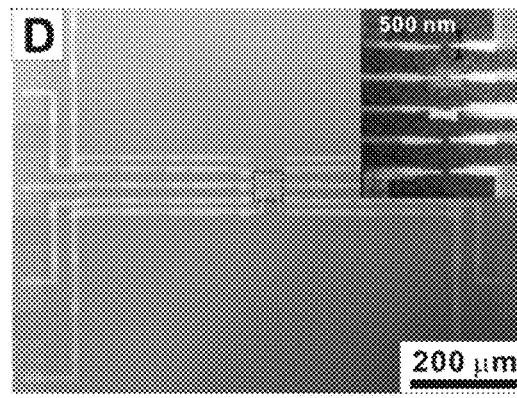
FIGURE 9D

NANOPATTERNED EXTRACELLULAR MATRICES ENABLE CELL-BASED ASSAYS WITH A MASS SPECTROMETRIC READOUT

CROSS REFERENCE TO RELATED APPLICATION

This application claims the benefit of U.S. Provisional Application Ser. No. 62/396,972, filed Sep. 20, 2016, the disclosure of which is incorporated herein by reference in its entirety.

STATEMENT OF GOVERNMENT INTEREST

This invention was made with government support under U54 CA199091 awarded by the National Institutes of Health and FA9550-12-1-0141 awarded by the Air Force Office of Scientific Research (AFOSR). The government has certain rights in this invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: 2016-156_Seqlisting.txt; Size: 739 bytes, created: Sep. 20, 2017.

FIELD OF THE INVENTION

The present disclosure provides methods in which adherent cells are treated with small molecules, cultured, lysed, and then analyzed by mass spectrometry to measure the activities of endogenous enzymes. The implementation of this method relies on the use of surfaces that are nanopatterned with cell adhesion ligands to mediate cell attachment and a peptide that is a substrate for the desired enzyme activity in the lysate.

BACKGROUND

Assays that evaluate the biological effects of small molecules in cell cultures are important in many applications including studying the mechanisms of action of natural products, elucidating signal transduction pathways, and screening small molecule libraries in drug discovery programs.[1,2] Yet, it is still difficult to measure many biochemical activities in cell-based assays, and therefore these assays cannot be applied to many targets of interest. Indeed, most assays report on a phenotypic behavior, including cell differentiation,[3] cell death,[4] and migration[5] and in those cases they do not measure the inhibition or activation of specific enzymes. Detection methods based on fluorescent proteins[6] have allowed the real-time observation of specific enzyme activities, but it remains challenging to develop these reagents and many biochemical activities have not yet been targeted with these approaches.

SUMMARY

The present disclosure generally provides a strategy wherein adherent cells are treated with small molecules, cultured, lysed, and then analyzed by mass spectrometry to measure the activities of endogenous enzymes. The implementation of this method relies on the use of surfaces that are nanopatterned with extracellular matrix (ECM) proteins to mediate cell attachment and a peptide that is a substrate for the desired enzyme activity in the lysate.

The approach described herein is based on monolayers having two distinct properties; they must present proteins that mediate cell adhesion, and they must also present peptides that are substrates for enzymes whose activities are being measured. Because these two functions are not compatible—since the adhesion proteins would obstruct access of the enzyme to the immobilized peptide—it is necessary to pattern the monolayer into two regions. By using the emerging state-of-the-art cantilever-free polymer pen lithography (PPL)[7-11] technique to create nanopatterns of the adhesive protein in 750 nm features, cells can still attach and spread but the majority of the monolayer then presents the phosphopeptide substrate that is measured by self-assembled monolayer laser desorption/ionization (SAMDI) mass spectrometry (FIGS. 1 and 2).[12] In this way, cells adhere to the surface by way of interactions with the matrix proteins,[13] while the other regions of the surface remain available for recording the enzyme activity (FIGS. 3A and 3B). A further benefit of this approach is that it can be used to define sites for adsorption of virtually any matrix protein and therefore it allows the tandem culture and lysis (TCAL-SAMDI) method to be applied to assays using any adherent cell line.[14]

Thus, in some aspects the disclosure provides a method of assaying activity of an intracellular enzyme, comprising (a) printing a surface with an array of immobilized cell adhesion ligands and immobilized substrates for the intracellular enzyme by (i) coating a polymer pen lithography (PPL) tip array with a first monolayer reagent and printing the first monolayer reagent at selected positions on the surface to form an array of printed first monolayer reagent, (ii) incubating the array of printed first monolayer reagent with a second monolayer reagent such that the second monolayer reagent is adsorbed onto unprinted portions of the surface, wherein one of the first monolayer reagent and the second monolayer reagent comprises a monolayer reagent for adsorption of the cell adhesion ligand and the other comprises a monolayer reagent for chemical immobilization of the substrate for the intracellular enzyme, (iii) contacting the resulting array of step (ii) with the substrate for the intracellular enzyme under conditions to immobilize the substrate to the surface at the portion of the surface comprising the monolayer reagent for chemical immobilization, (iv) contacting the resulting array of step (ii) with the cell adhesion ligand under conditions to immobilize the cell adhesion ligand to the surface at the portion of the surface comprising the monolayer reagent for adsorption of the cell adhesion ligand; wherein steps (iii) and (iv) can be performed in either order; (b) contacting a cell and the surface of step (a), the contacting resulting in immobilization of the cell via interaction between the cell and the immobilized cell adhesion ligand; (c) contacting the immobilized cell with a lysing solution to form a cell lysate and release the enzyme, thereby allowing contact between the enzyme and the immobilized substrate to transform the immobilized substrate to a product, the product having a different mass than the substrate; and (d) measuring the amount of the product formed using matrix-assisted laser desorption/ionization mass spectrometry (MALDI-MS) to assay the activity of the enzyme.

The disclosure also provides, in some embodiments, methods that further comprise washing the surface after immobilizing the cell on the surface and before lysing the cell to remove all cells not immobilized onto the surface.

In some embodiments, the surface comprises a second immobilized substrate that associates with a second enzyme in the cell lysate to form a second product, the second product having a different mass than the second substrate.

In further embodiments, the lysate comprises a potential modulator of binding of the enzyme and the immobilized substrate; and the activity of the enzyme assayed indicates the potential modulator's effect on the binding of the enzyme and the immobilized substrate in the presence of the potential modulator. In some embodiments, the lysate comprises a second potential modulator of binding of the second enzyme and the second immobilized substrate; and the activity of the second enzyme assayed indicates the second potential modulator's effect on the binding of the second enzyme and the second immobilized substrate in the presence of the second potential modulator. In further embodiments, the potential modulator or the second potential modulator is an inhibitor of the enzyme and immobilized substrate binding. In some embodiments, the potential modulator or the second potential modulator is an activator of the enzyme and immobilized substrate binding.

In some embodiments, the PPL tip array comprises a compressible elastomeric polymer comprising a plurality of non-cantilevered tips each having a radius of curvature of less than 1 μm and a common substrate comprising a compressible elastomeric polymer, the tip array and the common substrate mounted onto a rigid support and the tip array, common substrate, and rigid support together being at least translucent. In further embodiments, the compressible elastomeric polymer comprises polydimethylsiloxane (PDMS).

BRIEF DESCRIPTION OF THE FIGURES

FIG. 8 shows MHA dot size as a function of tip-surface contact time. Dot size increases with increasing tip-surface contact time at constant contact (pressure) (initial contact). The results were obtained using a polymer pen array with 15,000 pyramid-shaped tips at a temperature of 23° C. and relative humidity of 50% (circles) and 90% (squares).

FIGS. 9A-9D show (A) Optical image of a 480 μm×360 μm section of a one million gold dot array (6×6 within each block) on a silicon surface (using a pen array with 28,000 pyramid-shaped tips). (B) MHA dot size as a function of relative z-piezo extension. The results were obtained using a polymer pen array with 15,000 pyramid-shaped tips at 25° C. with a relative humidity of 40%. (C) Optical image of arrays of gold squares generated at different z-piezo extensions (using a pen array with 28,000 pyramid-shaped tips). (D) An optical microscope image of a multi-dimensional gold circuit fabricated by Polymer Pen Lithography. The inset shows a magnified image of the circuit center.

DESCRIPTION

Figure 1:
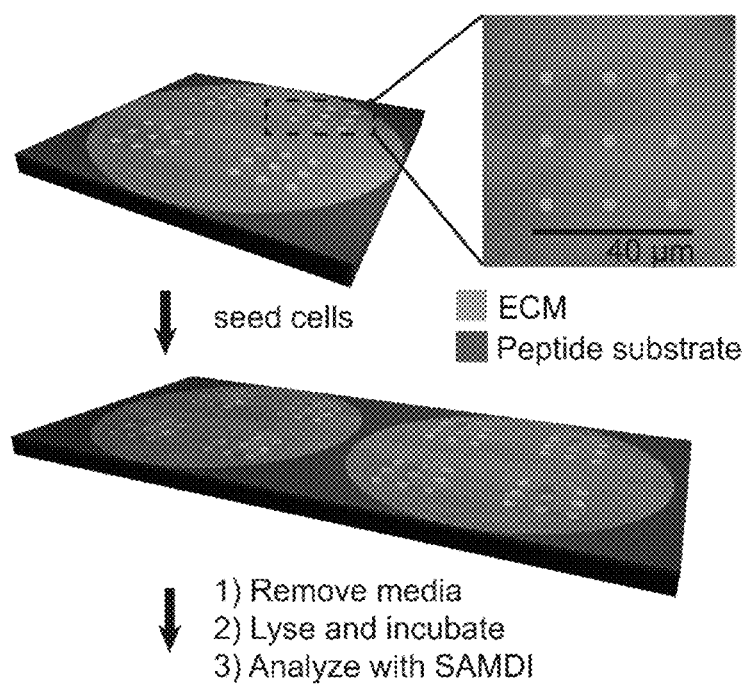
FIG. 1 shows work reports the use of surfaces that are nanopatterned with extracellular matrix proteins that support cell adhesion, and where the intervening regions present a peptide substrate for an enzyme, to enable cell-based assays using SAMDI mass spectrometry. Note that this work used nanoarrays that have 100 fibronectin features. Cells that are adherent to the nanoarrays are cultured and treated with small molecules. The media is then removed and a lysis buffer is applied to each region of cells, where enzymes in the lysate can modify the peptide in the intervening regions. The surface is then rinsed and analyzed with SAMDI mass spectrometry to determine the extent of conversion of the peptide substrate and therefore the amount of enzyme activity in the lysate.

The present disclosure describes methods for measuring enzyme activities, such as enzyme activities measured from a cell lysate. The methods are based on the SAMDI mass spectrometry technique (U.S. Patent Application Publication Number 2010/0112722, incorporated herein by reference in its entirety) and use matrix-assisted laser desorption-ionization mass spectrometry to analyze self-assembled monolayers. Polymer pen lithography (PPL) as described herein is also generally disclosed in International Application Number PCT/US2009/041738 (WO 2009/132321), which is incorporated by reference herein in its entirety.

Cell-based assays are finding wider use in evaluating compounds in primary screens for drug development, yet it is challenging to measure enzymatic activities as an end point in a cell-based assay. The present disclosure provides a cellular analysis strategy that combines cantilever free polymer pen lithography (PPL) with SAMDI mass spectrometry to guide cell localization and study enzymatic activity of the cells upon treatment with molecules from a drug library. The approach of using nanopatterning to mediate cell adhesion and SAMDI to record enzyme activities in the proximal lysate enables a broad range of cellular assays for applications in drug discovery and research not possible with conventional strategies.

Self-Assembled Monolayer Surfaces. The present disclosure contemplates the use of self-assembled monolayers as surfaces for assay applications (Mrksich et al., Annu Rev Biophys Biomol Struct 25: 55-78 (1996); Hodneland et al., Langmuir 13: 6001-6003 (1997); Houseman et al., FASEB J 11: A1095-A1095 (1997); Mrksich, Curr Opin Colloid In 2: 83-88 (1997); Mrksich et al., Acs Sym Ser 680: 361-373 (1997); Houseman et al., Mol Biol Cell 9: 430a-430a (1998); Mrksich, Cell Mol Life Sci 54: 653-662 (1998); Houseman et al., Angew Chem Int Ed 38: 782-785 (1999); Li et al., Langmuir 15: 4957-4959 (1999); Yousaf et al., J Am Chem Soc 121: 4286-4287 (1999); Houseman et al., Mol Biol Cell 11: 45a-45a (2000); Luk et al., Langmuir 16: 9604-9608. (2000); Mrksich, Chem Soc Rev 29: 267-273 (2000); Yousaf et al., Angew Chem Int Ed Engl 39: 1943-1946 (2000); Yousaf et al., Biochemistry 39: 1580-1580 (2000); Houseman et al., Biomaterials 22: 943-955 (2001); Kato et al., Biochemistry 40: 8608-8608 (2001); Yeo et al., Chembiochem 2: 590-593 (2001); Yousaf et al., Proc Natl Acad Sci USA 98: 5992-5996. (2001); Yousaf et al., Angew Chem Int Ed Engl 40: 1093-1096 (2001); Hodneland et al., Proc Natl Acad Sci USA 99: 5048-5052 (2002); Houseman et al., Nat Biotechnol 20: 270-274 (2002); Houseman et al., Top Curr Chem 218: 1-44 (2002); Houseman et al., Trends Biotechnol 20: 279-281 (2002); Houseman et al., Chem Biol 9: 443-454 (2002); Kwon et al., J Am Chem Soc 124: 806-812 (2002); Lee et al., Science 295: 1702-1705 (2002); Mrksich, Curr Opin Chem Biol 6: 794-797 (2002); Houseman et al., Langmuir 19: 1522-1531 (2003); Luk et al., Biochemistry 42: 8647-8647 (2003); Yeo et al., Angew Chem Int Ed Engl 42: 3121-3124 (2003); Dillmore et al., Langmuir 20: 7223-7231 (2004); Feng et al., Biochemistry 43: 15811-15821 (2004); Kato et al., J Am Chem Soc 126: 6504-6505 (2004); Min et al., Curr Opin Chem Biol 8: 554-558 (2004); Murphy et al., Langmuir 20: 1026-1030 (2004); Yeo et al., Adv Mater 16: 1352-1356 (2004); Yonzon et al., J Am Chem Soc 126: 12669-12676 (2004); Mrksich, MRS Bull 30: 180-184 (2005); James et al., Cell Motil Cytoskeleton 65: 841-852 (2008)). Previous work utilized a monolayer that presented a peptide against a background of tri(ethylene glycol) groups (Houseman et al., Nat Biotechnol 20: 270-274 (2002)). The peptide was a substrate for Src kinase and the glycol groups prevented non-specific adsorption of protein to the monolayer. Treatment of the monolayer with enzyme and ATP resulted in phosphorylation of the peptide, which was detected by measuring radioactivity from a $^{32}P$ label or by using an anti-phosphotyrosine antibody with detection by fluorescence scanning or surface plasmon resonance spectroscopy. This example showed that the use of monolayers gave solid-phase assay with exceptional performance. It further indicated that blocking procedures were unnecessary; the signal was 80-fold above background; and that enzyme constants and inhibitor dissociation constants could be measured quantitatively. The monolayers offer the benefits that immobilized ligands are presented in a homogeneous environment and the density of the immobilized ligands can be controlled and made uniform across the entire array (Gawalt et al., J Am Chem Soc 126: 15613-7 (2004)). The monolayers are also compatible with a range of immobilization chemistries (Montavon et al., Nat Chem 4: 45-51 (2012); Ban et al., Nat Chem Biol 8: 769-773 (2012); Li et al., Langmuir 23, 11826-11835 (2007)). In these respects, the monolayers are more effective as substrates in assay applications than is the nitrocellulose material, or even the common use of glass. A significant additional benefit of the monolayer substrates is that they can be analyzed by matrix-assisted laser desorption-ionization mass spectrometry (i.e., SAMDI mass spectrometry) and therefore provide a route to label-free assays of biochemical activities (Su et al., Langmuir 19: 4867-4870 (2003)).

Samdi Mass Spectrometry

SAMDI mass spectrometry can be used to detect the mass of a substrate or product. In this way, when the monolayer is treated with an enzyme that modifies the immobilized substrate, the resulting mass change of the immobilized product can be detected with mass spectrometry. The assay is applicable to a broad range of post-translational activities, can be performed in high throughput using plates having a number of distinct reaction zones (e.g., 1536 or 384) offering a throughput of about 50,000 assays per day, and is quantitative with Z-factors greater than 0.8. The assay can also be used to screen small molecule libraries to identify inhibitors or activators of enzymes.

In SAMDI, the monolayer is irradiated with a laser, which results in desorption of the products and substrates through dissociation of a thiolate-gold bond, but with little fragmentation of these molecules. Hence, the resulting spectra are straightforward to interpret. Assays using this SAMDI technique can be used on a range of enzyme activities, and are quantitative, compatible with complex lysates, and adaptable to high throughput formats (Ban et al., Nat Chem Biol 8: 769-773 (2012); Li et al., Langmuir 23: 11826-11835 (2007); Su et al., Langmuir 19: 4867-4870 (2003); Su et al., Angew Chem Int Ed Eng. 41: 4715-4718 (2002); Min et al., Angewandte Chemie 43: 5973-5977 (2004); Min et al., Anal Chem 76: 3923-3929 (2004); Yeo et al., Angew Chem Int Ed Engl 44: 5480-5483 (2005); Marin et al., Angew Chem Int Ed Engl 46: 8796-8798 (2007); Patrie et al., Anal Chem 79: 5878-5887 (2007); Ban et al., Angew Chem Int Ed Eng 47: 3396-3399 (2008); Gurard-Levin et al., Annu Rev Anal Chem (Palo Alto Calif) 1: 767-800 (2008); Gurard-Levin et al., Biochemistry 47: 6242-6250 (2008); Mrksich, ACS Nano 2: 7-18 (2008); Tsubery et al., Langmuir 24: 5433-5438 (2008); Gurard-Levin et al., Chembiochem 10: 2159-2161 (2009); Liao et al., Chemistry 15, 12303-12309 (2009); Gurard-Levin et al., ACS Chem Biol 5: 863-873 (2010); Kim et al., Nucleic Acids Res 38: e2 (2010); Cai et al., Carbohydr Res 346: 1576-1580 (2011); Gurard-Levin et al., ACS Comb Sci 13: 347-350 (2011); Liao et al., Angew Chem Int Ed Engl 50: 706-708 (2011); Prats-Alfonso et al., Small 8: 2106-2115 (2012); Li et al., Langmuir 29: 294-298 (2013)).

In general, the disclosure provides methods of assaying activity of an intracellular enzyme, comprising (a) contacting a cell and a surface, the surface comprising an immobilized cell adhesion ligand and an immobilized substrate for the enzyme, the contacting resulting in immobilization of the cell via interaction between the cell and the immobilized cell adhesion ligand; (b) contacting the cell with a lysing solution to form a cell lysate and release the enzyme, thereby allowing contact between the enzyme and the immobilized substrate to transform the immobilized substrate to a product, the product having a different mass than the substrate; and (c) measuring the amount of the product formed using matrix-assisted laser desorption/ionization mass spectrometry (MALDI-MS) to assay the activity of the enzyme.

The methods described herein offer several advantages over existing technologies. First, the assay provides a way to acquire enzyme activity measurements from thousands of independently generated cell lysates. Existing screening assays frequently use gene expression or phenotypic changes as a readout. Next, the assay uses self-assembled monolayers for culturing cells and for reporting on enzyme activities from lysates generated by the cultured cells. This unique combination enables quantitative readouts of enzyme activities in a high throughput format. Further, the assay is label-free, whereas most screening assays require a labeled reporter. Also, the assay is easily adapted to new targets. As disclosed herein, this is achieved by simply immobilizing a substrate for the enzyme of interest onto the monolayer. Also as disclosed herein the assay requires only a small number of cells for various enzyme activities. Finally, the assay can measure activities from enzymes, such as phosphatases, which are impractical to measure in high-throughput from cell lysates using other assay technologies.

Cell-based screening is an increasingly popular tool used in drug discovery. This technology opens up the potential of conducting cell-based screens that use enzyme activity measurements as the readout. This is of significant value because cell-based screens provide more physiologically relevant information about the activity of compounds, potentially leading to better lead compounds in drug discovery efforts.

TCAL-SAMDI as disclosed herein provides a general method for conducting cell-based, chemical screening with quantitative readouts of enzymatic activity, easily adaptable to a wide range of targets.

Monolayer Reagent: The monolayer on the surface is prepared in two steps—(1) patterning a first monolayer reagent onto selection sections of the surface then (2) incubating the second monolayer reagent so as to adhere to the unpatterned sections of the surface—thereby creating a surface covered in monolayer reagent(s). The first monolayer can be the reagent that is capable of adsorption of the cell adhesion ligand or the reagent that is capable of chemical immobilization of the substrate for the intracellular enzyme to be assayed. The second monolayer reagent is the reagent not used in the first (PPL patterning) step.

A monolayer reagent capable of adsorption of the cell adhesion ligand is a monolayer reagent for nonspecific adsorption of protein. In some cases, such a monolayer reagent has a structure of $HS(CH_2)_nX$, where n is 8-20 and X is methyl, OH, $OC_{1-3}$alkyl, $CO_2H$, or $NH_2$. More specific examples of such monolayer reagents include mercaptohexadecanoic acid (MHA), a $C_{8-20}$ hydroxyalkane, and hexadecane thiolate.

A monolayer reagent capable of chemical immobilization of the substrate for the intracellular enzyme is a reagent comprising a compatible reactive chemical moiety to the substrate in order to form a chemical (covalent) bond. For example, the reagent can comprise an alkyne and the substrate an azide (or vice versa) to form a triazole (e.g., click chemistry). The reagent can comprise an amine and the substrate a carboxyl group (e.g., a carboxylic acid, an anhydride, or an acid chloride) (or vice versa) to form an amide bond. The reagent can comprise a maleimide and the substrate a thiol (or vice versa) to form an alpha-carbon substituted imide. Other reactive pairs can be used between the substrate and reagent to form a chemical bond. The reagent comprises the immobilizing moiety (the reactive chemical moiety for reaction with the substrate) and further comprises an inert moiety. The inert moiety can comprise mannitol and/or 3-6 ethylene glycol units (e.g., $(CH_2CH_2O)_{3-6}$). See, e.g., Luk, et al., *Langmuir*, 16:9604-9608 (2000).

The monolayer reagent can be bound to the surface via a thiol bond (e.g., the monolayer reagent comprises a thiol —SH— and reacts with the surface to form a bond via the sulfur atom). In some cases, the monolayer reagent can further comprise a linker. For example, the linker can have a structure of formula (I)

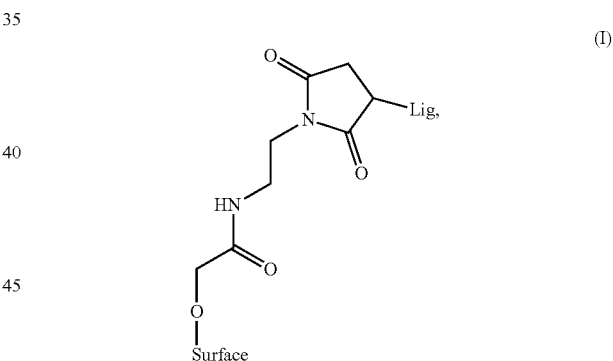

where Lig comprises the cell adhesion ligand or the immobilized substrate.

Lysing Solution. As discussed herein, methods of the disclosure involve contacting a cell with a lysing solution (i.e., lysis buffer). Solutions that will lyse cells (e.g., any prokaryotic, eukaryotic, or plant cell) are well known in the art. Lysis buffers contemplated herein comprise, in various embodiments, a detergent to effect lysis of the cell of interest. Detergents are a class of molecules whose unique properties enable manipulation (e.g., disruption or formation) of hydrophobic-hydrophilic interactions among molecules in biological samples. It is contemplated herein that detergents are used to lyse cells through solubilization of membrane proteins and lipids to release the cell contents.

Detergents are amphipathic molecules, meaning they contain both a nonpolar "tail" having aliphatic or aromatic character and a polar "head." Ionic character of the polar head group forms the basis for broad classification of detergents; they may be ionic (charged, either anionic (e.g., sodium dodecyl sulfate (SDS) or cationic (e.g., ethyl trimethyl ammonium bromide), nonionic (uncharged; e.g., NP-40, Brij-35, Brij-58, Tween20, Tween80, octyl glucoside, octyl thioglucoside) or zwitterionic (having both positively and negatively charged groups but with a net charge of zero; e.g., CHAPS, CHAPSO). Detergents can be denaturing or non-denaturing with respect to protein structure. Denaturing detergents can be anionic such as sodium dodecyl sulfate (SDS) or cationic such as ethyl trimethyl ammonium bromide. Non-denaturing detergents can be divided into nonionic detergents such as Triton X-100, bile salts such as cholate and zwitterionic detergents such as CHAPS. Lysis buffers also comprise, in various embodiments, salts such as Tris-HCl and/or EDTA to regulate the acidity and osmolarity of the lysate.

Surface. The surface can be any material capable of forming a monolayer, e.g., a monolayer of alkanethiols. Particularly, the substrate may be a metal, such as Au, Ag, Pd, Pt, Cu, Zn, Fe, In, Si, $Fe_2O_3$, $SiO_2$ or ITO (indium tin oxide) glass. In various embodiments, the disclosure contemplates that a surface useful in the methods described herein comprises Au, Ag, or Cu.)

Cell Adhesion Ligand. As discussed herein, aspects of the disclosure contemplate the use of a surface comprising an immobilized cell adhesion ligand. In various embodiments, the cell adhesion ligand comprises an amino acid sequence such as, for example and without limitation, RGD or GRTY (SEQ ID NO: 1). In some embodiments, the cell adhesion ligand comprises an extracellular matrix (ECM) protein, including but not limited to fibronectin, collagen, elastin, and laminin.

Immobilized Substrate. In various aspects, the disclosure contemplates a surface, the surface comprising an immobilized cell adhesion ligand and an immobilized substrate for an enzyme. In general, the substrate for an enzyme of interest is known in the art. For example and without limitation, if the enzyme of interest is a phosphatase, then the immobilized substrate can be a peptide sequence comprising a phosphorylated amino acid. The substrate is immobilized to the surface via the monolayer reagent for chemical immobilization, as discussed above.

Intracellular Enzyme. The disclosure generally provides methods of assaying activity of an intracellular enzyme. Any enzyme is contemplated for use according to the methods provided herein, including but not limited to a deacetylase, acetyltransferase, esterase, phosphorylase/kinase, phosphatase, protease, methylase, demethylase, or a DNA or RNA modifying enzyme.

High Throughput Formats for SAMDI. An improvement to the SAMDI method is disclosed herein. The improved method translates SAMDI to a high throughput format based on standard 384 and 1536 microtiter plate formats. This format uses a stainless steel plate in the size of a microtiter plate and having an array of gold-coated islands modified with a monolayer presenting maleimide groups (e.g., linkers of formula I) against a background of tri(ethylene glycol) groups. Substrates are then immobilized to each of the islands; in various embodiments, in a high throughput screen each island has the same substrate whereas in an experiment to identify active substrates for an enzyme each spot would present a different substrates (or suspected substrates). Standard robotic liquid handling equipment can be used to prepare arrays of reactions and to transfer those reaction mixtures to the array plates. The treated plates are incubated (e.g., between 30-60 minutes), washed, and a solution of matrix is applied to the surface. The plate is then loaded into a MALDI-ToF instrument, and each spot is analyzed in an automated fashion in approximately 30 minutes. Resulting data is analyzed using custom written software that can compare the location and magnitude of the peaks in the SAMDI spectra to a reference mass file unique to each set of peptides to look for specific reaction profiles based on characteristic mass shifts (i.e., −42 for deacetylation, +80 for phosphorylation, +14 for methylation). The software presents the data in a manner that can be further analyzed with standard commercial packages (such as Excel) to identify hits in a high throughput screen, or to generate heatmaps of activities. Recent work has demonstrated the screening of 100,000 molecules against the KDAC8 deacetylase (Gurard-Levin et al., ACS Comb Sci 13: 347-350 (2011)).

Modulators/Activators. As described herein, various aspects of the disclosure provide a method of assaying activity of an intracellular enzyme, comprising (a) contacting a cell and a surface, the surface comprising an immobilized cell adhesion ligand and an immobilized substrate for the enzyme, the contacting resulting in immobilization of the cell via interaction between the cell and the immobilized cell adhesion ligand; (b) contacting the cell with a lysing solution to form a cell lysate and release the enzyme, thereby allowing contact between the enzyme and the immobilized substrate to transform the immobilized substrate to a product, the product having a different mass than the substrate; and (c) measuring the amount of the product formed using matrix-assisted laser desorption/ionization mass spectrometry (MALDI-MS) to assay the activity of the enzyme. In some embodiments, the assay is performed in the presence of one or more potential modulators of the enzyme-substrate binding; subjecting the substrate and product to mass spectrometry to produce a mass spectrum having a product signal and a substrate signal; and binding of the enzyme and the immobilized substrate is detected by correlating a signal intensity of the product to a signal intensity of the substrate to determine the extent of product formation and thereby detecting the binding of the enzyme and the immobilized substrate in the presence of the one or more potential modulators.

In some embodiments, the modulator is an inhibitor of the enzyme and immobilized substrate binding. In further embodiments, the modulator is an activator of the enzyme and immobilized substrate binding.

Multiplexing. As described and exemplified herein, the methods of the disclosure are amenable to the multiplex format. Thus, in any of the aspects or embodiments of the disclosure, simultaneous analysis of more than one immobilized substrate is contemplated. In further embodiments, the more than one immobilized substrate is analyzed directly from a cell lysate following lysis of one or more cells on a surface.

Polymer Pen Lithography

Figure 5A:
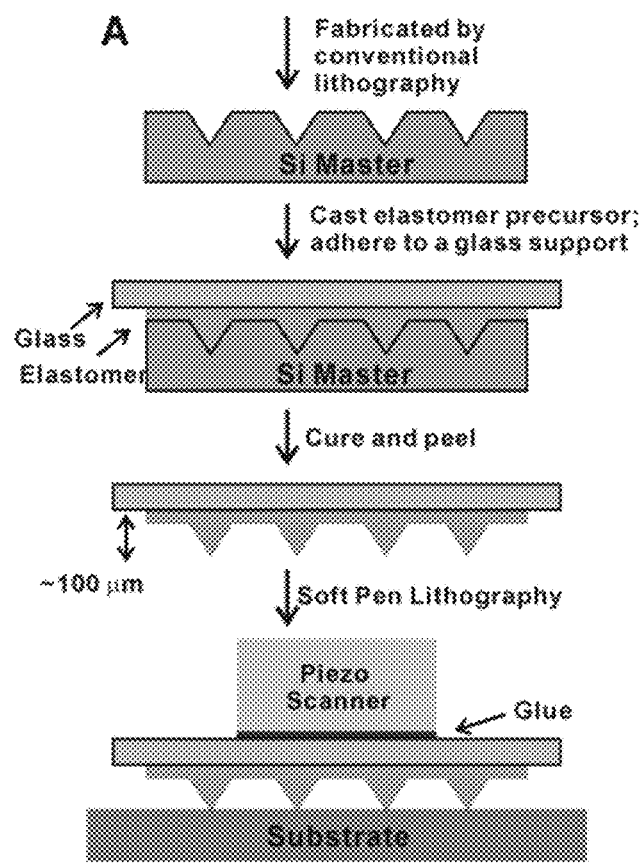
FIGS. 5A-5C show (A) A schematic illustration of the Polymer Pen Lithography setup. (B) A photograph of a 11 million pen array. (C) SEM image of the polymer pen array. The average tip radius of curvature is 70±10 nm (inset).
Figure 5B:
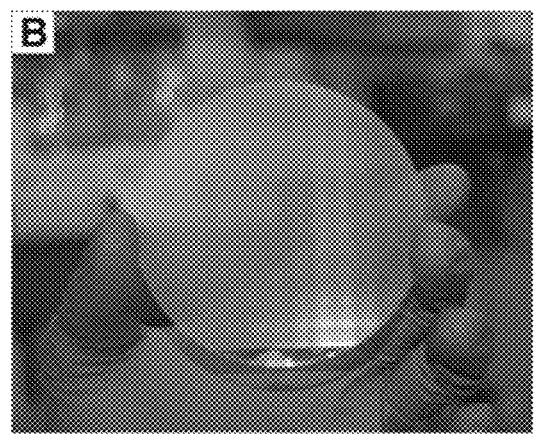

Polymer Pen Lithography is generally disclosed in International Application No. PCT/US09/041738 (WO 09/132321), and is a direct-write method that delivers collections of molecules in a positive printing mode. In contrast with DPN and other SPM-based lithographies, which typically use hard silicon-based cantilevers, Polymer Pen Lithography utilizes elastomeric tips without cantilevers) as the ink delivery tool. The tips are preferably made of polydimethylsiloxane, PDMS. A preferred polymer pen array (FIGS. 5A-5C) contains thousands of tips, preferably having a pyramidal shape, which can be made with a master prepared by conventional photolithography and subsequent wet chemical etching (FIG. 5A). The tips preferably are connected by a common substrate which includes a thin polymer backing layer (50-100 μm thick), which preferably is adhered to a rigid support (e.g., a glass, silicon, quartz, ceramic, polymer, or any combination thereof), e.g. prior to or via curing of the polymer. The rigid support is preferably highly rigid and has a highly planar surface upon which to mount the array (e.g., silica glass, quartz, and the like). The rigid support and thin backing layer significantly improve the uniformity of the polymer pen array over large areas, such as three inch wafer surface (FIG. 5B), and make possible the leveling and uniform, controlled use of the array. When the sharp tips of the polymer pens are brought in contact with a substrate, ink is delivered at the points of contact (FIG. 5A).

The amount of light reflected from the internal surfaces of the tips increases significantly when the tips make contact with the substrate. Therefore, a translucent or transparent elastomer polymer pen array allows one to visually determine when all of the tips are in contact with an underlying substrate, permitting one to address the otherwise daunting task of leveling the array in an experimentally straightforward manner. Thus, preferably one or more of the array tips, backing layer, and rigid support are at least translucent, and preferably transparent.

Figure 5C:
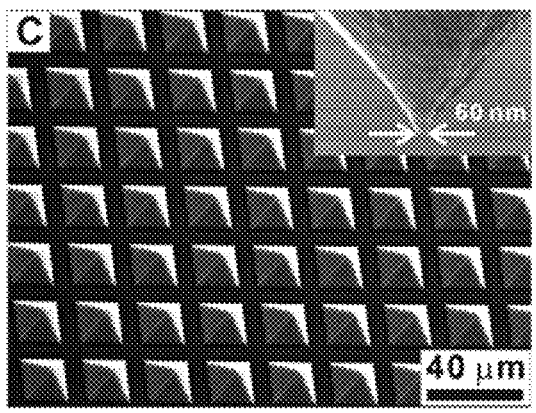
Figure 6:
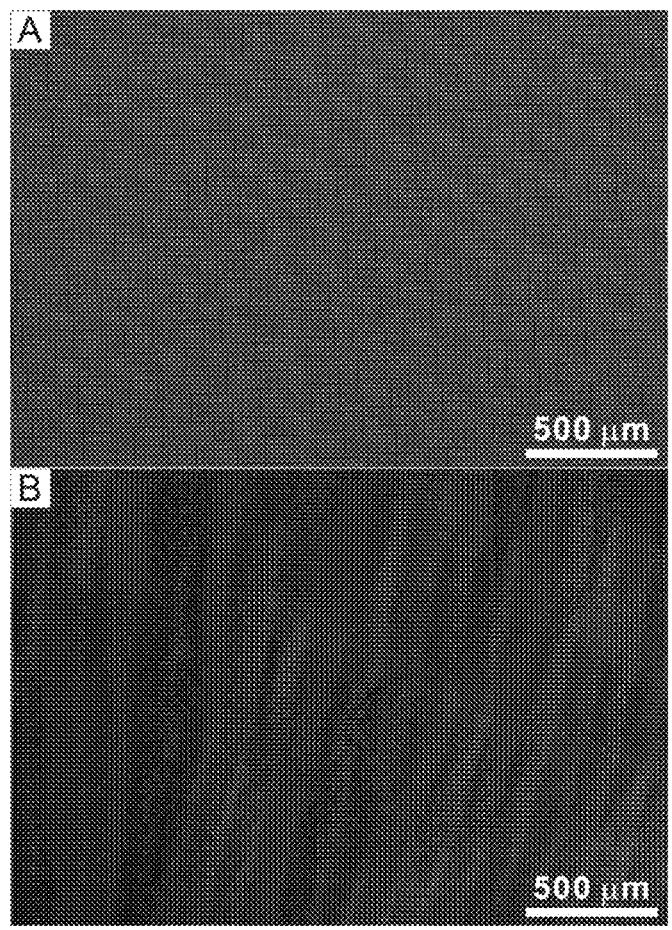
FIG. 6 shows SEM images of a polymer pen array (A) with and (B) without a glass support. The polymer pen array with a glass support is uniform across the whole area, while the one without a glass support is wavy.
Figure 7:
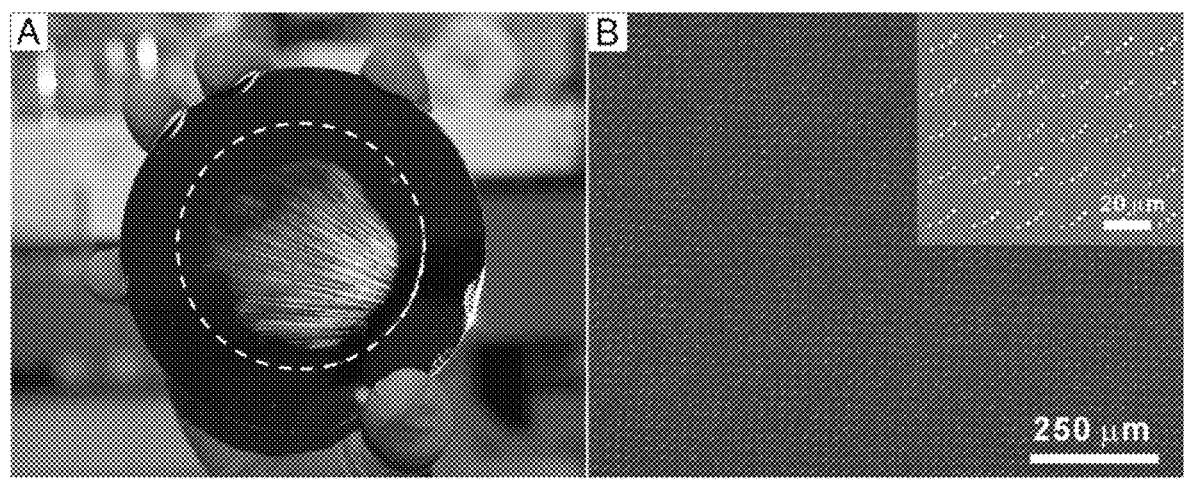
FIG. 7 shows (A) A photograph of an etched gold pattern on a 4 inch Si wafer fabricated by Polymer Pen Lithography using the 11-million pen array shown in FIG. 1B. The area patterned by the pen array is highlighted with a white dashed line. In the center of the pen array, greater than 99% of the pens uniformly deliver the MHA ink to the surface during the Polymer Pen Lithography process and form well-defined structures. Reduced activity occurs on the periphery of the array, due to poor contact between the pens in the peripheral area of the array and the Si surface. This arises from current instrument sample holder limitations. (B) Optical microscope image of gold patterns in (A) made by Polymer Pen Lithography. The inset is a zoom-in image. The image shows that every intended structure forms in this experiment.

Depending upon intended use, the pitch of a pen array is deliberately set between 20 μm and 1 mm, corresponding to pen densities of 250,000/cm² and 100/cm², respectively. Larger pitch arrays are required to make large features (micron or millimeter scale) but also can be used to make nanometer scale features. All of the pens were remarkably uniform in size and shape, with an average tip radius of 70±10 nm (FIG. 5C). In principle, this value can be reduced substantially with higher quality masters and stiffer elastomers. For the examples below, the tip array used contained either 15,000 or 28,000 pyramid-shaped pens, but arrays with as many as about 11,000,000 pens have also been used to pattern structures (FIG. 7).

In a typical experiment, a pen array (1 cm² in size) can be inked by immersing it in a saturated solution of a desired material, e.g., 16-mercaptohexadecanoic acid (MHA) in ethanol, for five minutes followed by rinsing, e.g., with ethanol. The inked pen array can be used for to generate patterns on a substrate by bringing it in contact with the surface for a period of time (e.g., 0.1 s). This process of contacting the substrate can be repeated to generate an array of patterns (e.g., dots) with less than 10% deviation in feature diameter.

A defining characteristic of Polymer Pen Lithography, in contrast with DPN and most contact printing strategies which are typically viewed as pressure or force-independent, is that it exhibits both time- and pressure-dependent ink transport. As with DPN, features made by Polymer Pen Lithography exhibit a size that is linearly dependent on the square root of the tip-substrate contact time (FIG. 8). This property of Polymer Pen Lithography, which is a result of the diffusive characteristics of the ink and the small size of the delivery tips, allows one to pattern sub-micron features with high precision and reproducibility (variation of feature size is less than 10% under the same experimental conditions). The pressure dependence of Polymer Pen Lithography derives from the compressible nature of the elastomer pyramid array. Indeed, the microscopic, preferably pyramidal, tips can be made to deform with successively increasing amounts of applied pressure, which can be controlled by simply extending the piezo in the vertical direction (z-piezo). Although such deformation has been regarded as a major drawback in contact printing (it can result in "roof" collapse and limit feature size resolution), with Polymer Pen Lithography, the controlled deformation can be used as an adjustable variable, allowing one to control tip-substrate contact area and resulting feature size. Within the pressure range allowed by z-piezo extension of about 5 to about 25 μm, one can observe a near linear relationship between piezo extension and feature size at a fixed contact time of 1 s (FIG. 9B). Interestingly, at the point of initial contact and up to a relative extension 0.5 μm, the sizes of the patterned dots do not significantly differ and are both about 500 nm, indicating that the backing elastomer layer, which connects all of the pyramids, deforms before the pyramid-shaped tips do. This type of buffering is fortuitous and essential for leveling because it provides extra tolerance in bringing all of the tips in contact with the surface without tip deformation and significantly changing the intended feature size. When the z-piezo extends 1 μm or more, the tips exhibit a significant and controllable deformation (FIG. 9B).

With the pressure dependency of Polymer Pen Lithography, one does not have to rely on the time-consuming, meniscus-mediated ink diffusion process to generate large features. Indeed, one can generate either nanometer or micrometer sized features in only one printing cycle by simply adjusting the degree of tip deformation.

Note that the maskless nature of Polymer Pen Lithography allows one to arbitrarily make many types of structures without the hurdle of designing a new master via a throughput-impeded serial process.

Polymer Pen Lithography merges many of the attributes of DPN and contact printing to yield patterning capabilities that span multiple length scales with high throughput and low cost. The time- and pressure-dependent ink transport properties of the polymer pen pyramid arrays provide important and tunable variables that distinguish Polymer Pen Lithography from the many nano- and microfabrication approaches that have been developed to date.

Tip Arrays

The lithography methods disclosed herein employ a tip array formed from elastomeric polymer material. The tip arrays are non-cantilevered and comprise tips which can be designed to have any shape or spacing between them, as needed. The shape of each tip can be the same or different from other tips of the array. Contemplated tip shapes include spheroid, hemispheroid, toroid, polyhedron, cone, cylinder, and pyramid (trigonal or square). The tips are sharp, so that they are suitable for forming submicron patterns, e.g., less than about 500 nm. The sharpness of the tip is measured by its radius of curvature, and the radius of curvature of the tips disclosed herein is below 1 μm, and can be less than about 0.9 μm, less than about 0.8 μm, less than about 0.7 μm, less than about 0.6 μm, less than about 0.5 μm, less than about 0.4 μm, less than about 0.3 μm, less than about 0.2 μm, less than about 0.1 μm, less than about 90 nm, less than about 80 nm, less than about 70 nm, less than about 60 nm, or less than about 50 nm.

The tip array can be formed from a mold made using photolithography methods, which is then used to fashion the tip array using a polymer as disclosed herein. The mold can be engineered to contain as many tips arrayed in any fashion desired. The tips of the tip array can be any number desired, and contemplated numbers of tips include about 1000 tips to about 15 million tips, or greater. The number of tips of the tip array can be greater than about 1 million, greater than about 2 million, greater than about 3 million, greater than about 4 million, greater than 5 million tips, greater than 6 million, greater than 7 million, greater than 8 million, greater than 9 million, greater than 10 million, greater than 11 million, greater than 12 million, greater than 13 million, greater than 14 million, or greater than 15 million tips.

The tips of the tip array can be designed to have any desired thickness, but typically the thickness of the tip array is about 50 nm to about 1 µm, about 50 nm to about 500 nm, about 50 nm to about 400 nm, about 50 nm to about 300 nm, about 50 nm to about 200 nm, or about 50 nm to about 100 nm.

The polymers can be any polymer having a compressibility compatible with the lithographic methods. Polymeric materials suitable for use in the tip array can have linear or branched backbones, and can be crosslinked or non-crosslinked, depending upon the particular polymer and the degree of compressibility desired for the tip. Cross-linkers refer to multi-functional monomers capable of forming two or more covalent bonds between polymer molecules. Non-limiting examples of cross-linkers include such as trimethylolpropane trimethacrylate (TMPTMA), divinylbenzene, di-epoxies, tri-epoxies, tetra-epoxies, di-vinyl ethers, tri-vinyl ethers, tetra-vinyl ethers, and combinations thereof.

Thermoplastic or thermosetting polymers can be used, as can crosslinked elastomers. In general, the polymers can be porous and/or amorphous. A variety of elastomeric polymeric materials are contemplated, including polymers of the general classes of silicone polymers and epoxy polymers. Polymers having low glass transition temperatures such as, for example, below 25° C. or more preferably below −50° C., can be used. Diglycidyl ethers of bisphenol A can be used, in addition to compounds based on aromatic amine, triazine, and cycloaliphatic backbones. Another example includes Novolac polymers. Other contemplated elastomeric polymers include methylchlorosilanes, ethylchlorosilanes, and phenylchlorosilanes, polydimethylsiloxane (PDMS). Other materials include polyethylene, polystyrene, polybutadiene, polyurethane, polyisoprene, polyacrylic rubber, fluorosilicone rubber, and fluoroelastomers.

Further examples of suitable polymers that may be used to form a tip can be found in U.S. Pat. Nos. 5,776,748; 6,596,346; and 6,500,549, each of which is hereby incorporated by reference in its entirety. Other suitable polymers include those disclosed by He et al., *Langmuir* 2003, 19, 6982-6986; Donzel et al., *Adv. Mater.* 2001, 13, 1164-1167; and Martin et al., *Langmuir*, 1998, 14-15, 3791-3795. Hydrophobic polymers such as polydimethylsiloxane can be modified either chemically or physically by, for example, exposure to a solution of a strong oxidizer or to an oxygen plasma.

The polymer of the tip array has a suitable compression modulus and surface hardness to prevent collapse of the polymer during inking and printing, but too high a modulus and too great a surface hardness can lead to a brittle material that cannot adapt and conform to a substrate surface during printing. As disclosed in Schmid, et al., *Macromolecules*, 33:3042 (2000), vinyl and hydrosilane prepolymers can be tailored to provide polymers of different modulus and surface hardness. Thus, in some cases, the polymer is a mixture of vinyl and hydrosilane prepolymers, where the weight ratio of vinyl prepolymer to hydrosilane crosslinker is about 5:1 to about 20:1, about 7:1 to about 15:1, or about 8:1 to about 12:1.

The polymers of the tip array preferably will have a surface hardness of about 0.2% to about 3.5% of glass, as measured by resistance of a surface to penetration by a hard sphere with a diameter of 1 mm, compared to the resistance of a glass surface (as described in Schmid, et al., *Macromolecules*, 33:3042 (2000) at p 3044). The surface hardness can be about 0.3% to about 3.3%, about 0.4% to about 3.2%, about 0.5% to about 3.0%, or about 0.7% to about 2.7%. The polymers of the tip array can have a compression modulus of about 10 MPa to about 300 MPa. The tip array preferably comprises a compressible polymer which is Hookean under pressures of about 10 MPa to about 300 MPa. The linear relationship between pressure exerted on the tip array and the feature size allows for control of the indicia printed using the disclosed methods and tip arrays (see FIG. 9B).

The tip array can comprise a polymer that has adsorption and/or absorption properties for the patterning composition, such that the tip array acts as its own patterning composition reservoir. For example, PDMS is known to adsorb patterning inks, see, e.g., US Patent Publication No. 2004/228962, Zhang, et al., *Nano Lett.* 4, 1649 (2004), and Wang et al., *Langmuir* 19, 8951 (2003).

The tip array can comprise a plurality of tips fixed to a common substrate and formed from a polymer as disclosed herein. The tips can be arranged randomly or in a regular periodic pattern (e.g., in columns and rows, in a circular pattern, or the like). The tips can all have the same shape or be constructed to have different shapes. The common substrate can comprise an elastomeric layer, which can comprise the same polymer that forms the tips of the tip array, or can comprise an elastomeric polymer that is different from that of the tip array. The elastomeric layer can have a thickness of about 50 µm to about 100 µm. The tip array can be affixed or adhered to a rigid support (e.g., glass, such as a glass slide). In various cases, the common substrate, the tip array, and/or the rigid support, if present, is translucent or transparent. In a specific case, each is translucent or transparent. The thickness of combination of the tip array and common substrate, can be less than about 200 µm, preferably less than about 150 µm, or more preferably about 100 µm.

Patterning Compositions

Patterning compositions suitable for use in the disclosed methods include both homogeneous and heterogeneous compositions, the latter referring to a composition having more than one component. The patterning composition is coated on the tip array. The term "coating," as used herein, refers both to coating of the tip array as well adsorption and absorption by the tip array of the patterning composition. Upon coating of the tip array with the patterning composition, the patterning composition can be patterned on a substrate surface using the tip array.

Patterning compositions can be liquids, solids, semi-solids, and the like. Patterning compositions suitable for use include, but are not limited to, molecular solutions, polymer solutions, pastes, gels, creams, glues, resins, epoxies, adhesives, metal films, particulates, solders, etchants, and combinations thereof.

Patterning compositions can include materials such as, but not limited to, monolayer-forming species, thin film-forming species, oils, colloids, metals, metal complexes, metal oxides, ceramics, organic species (e.g., moieties comprising a carbon-carbon bond, such as small molecules, polymers, polymer precursors, proteins, antibodies, and the like), polymers (e.g., both non-biological polymers and biological polymers such as single and double stranded DNA, RNA, and the like), polymer precursors, dendrimers, nanoparticles, and combinations thereof. In some embodiments, one or more components of a patterning composition includes a functional group suitable for associating with a substrate, for example, by forming a chemical bond, by an ionic interaction, by a Van der Waals interaction, by an electrostatic interaction, by magnetism, by adhesion, and combinations thereof. The patterning composition can be a monolayer reagent, e.g., a reagent that forms a monolayer. One contemplated monolayer reagent is MHA.

In some embodiments, the composition can be formulated to control its viscosity. Parameters that can control ink viscosity include, but are not limited to, solvent composition, solvent concentration, thickener composition, thickener concentration, particles size of a component, the molecular weight of a polymeric component, the degree of cross-linking of a polymeric component, the free volume (i.e., porosity) of a component, the swellability of a component, ionic interactions between ink components (e.g., solvent-thickener interactions), and combinations thereof.

In some embodiments, the patterning composition comprises an additive, such as a solvent, a thickening agent, an ionic species (e.g., a cation, an anion, a zwitterion, etc.) the concentration of which can be selected to adjust one or more of the viscosity, the dielectric constant, the conductivity, the tonicity, the density, and the like.

Suitable thickening agents include, but are not limited to, metal salts of carboxyalkylcellulose derivatives (e.g., sodium carboxymethylcellulose), alkylcellulose derivatives (e.g., methylcellulose and ethylcellulose), partially oxidized alkylcellulose derivatives (e.g., hydroxyethylcellulose, hydroxypropylcellulose and hydroxypropylmethylcellulose), starches, polyacrylamide gels, homopolymers of poly-N-vinylpyrrolidone, poly(alkyl ethers) (e.g., polyethylene oxide, polyethylene glycol, and polypropylene oxide), agar, agarose, xanthan gums, gelatin, dendrimers, colloidal silicon dioxide, lipids (e.g., fats, oils, steroids, waxes, glycerides of fatty acids, such as oleic, linoleic, linolenic, and arachidonic acid, and lipid bilayers such as from phosphocholine) and combinations thereof. In some embodiments, a thickener is present in a concentration of about 0.5% to about 25%, about 1% to about 20%, or about 5% to about 15% by weight of a patterning composition.

Suitable solvents for a patterning composition include, but are not limited to, water, C1-C8 alcohols (e.g., methanol, ethanol, propanol and butanol), C6-C12 straight chain, branched and cyclic hydrocarbons (e.g., hexane and cyclohexane), C6-C14 aryl and aralkyl hydrocarbons (e.g., benzene and toluene), C3-C10 alkyl ketones (e.g., acetone), C3-C10 esters (e.g., ethyl acetate), C4-C10 alkyl ethers, and combinations thereof. In some embodiments, a solvent is present in a concentration of about 1% to about 99%, about 5% to about 95%, about 10% to about 90%, about 15% to about 95%, about 25% to about 95%, about 50% to about 95%, or about 75% to about 95% by weight of a patterning composition.

In some embodiments, the patterning composition includes a reactive component. As used herein, a "reactive component" refers to a compound or species that has a chemical interaction with a substrate. In some embodiments, a reactive component in the ink penetrates or diffuses into the substrate. In some embodiments, a reactive component transforms, binds, or promotes binding to exposed functional groups on the surface of the substrate. Reactive components can include, but are not limited to, ions, free radicals, metals, acids, bases, metal salts, organic reagents, and combinations thereof. Reactive components further include, without limitation, monolayer-forming species such as thiols, hydroxides, amines, silanols, siloxanes, and the like, and other monolayer-forming species known to a person or ordinary skill in the art. The reactive component can be present in a concentration of about 0.001% to about 100%, about 0.001% to about 50%, about 0.001% to about 25%, about 0.001% to about 10%, about 0.001% to about 5%, about 0.001% to about 2%, about 0.001% to about 1%, about 0.001% to about 0.5%, about 0.001% to about 0.05%, about 0.01% to about 10%, about 0.01% to about 5%, about 0.01% to about 2%, about 0.01% to about 1%, about 10% to about 100%, about 50% to about 99%, about 70% to about 95%, about 80% to about 99%, about 0.001%, about 0.005%, about 0.01%, about 0.1%, about 0.5%, about 1%, about 2%, or about 5% weight of the patterning composition.

The patterning composition can include a masking component. As used herein, a "masking component" refers to a compound or species that upon reacting forms a surface feature resistant to a species capable of reacting with the surrounding surface. Masking components suitable for use with the present invention include materials commonly employed in traditional photolithography methods as "resists" (e.g., photoresists, chemical resists, self-assembled monolayers, etc.). Masking components suitable for use in the disclosed methods include, but are not limited to, a polymer such as a polyvinylpyrollidone, poly(epichlorohydrin-co-ethyleneoxide), a polystyrene, a poly(styrene-co-butadiene), a poly(4-vinylpyridine-co-styrene), an amine terminated poly(styrene-co-butadiene), a poly(acrylonitrile-co-butadiene), a styrene-butadiene-styrene block copolymer, a styrene-ethylene-butylene block linear copolymer, a polystyrene-block-poly(ethylene-ran-butylene)-block-polystyrene, a poly(styrene-co-maleic anhydride), a polystyrene-block-poly(ethylene-ran-butylene)-block-polystyrene-graft-mal-eic anhydride, a polystyrene-block-polyisoprene-block-polystyrene, a polystyrene-block-poly(ethylene-ran-butylene)-block-polystyrene, a polynorbornene, a dicarboxy terminated poly(acrylonitrile-co-butadiene-co-acrylic acid), a dicarboxy terminated poly(acrylonitrile-co-butadiene), a polyethyleneimine, a poly(carbonate urethane), a poly(acrylonitrile-co-butadiene-co-styrene), a poly(vinylchloride), a poly(acrylic acid), a poly(methylmethacrylate), a poly(methyl methacrylate-co-methacrylic acid), a polyisoprene, a poly(1,4-butylene terephthalate), a polypropylene, a poly(vinyl alcohol), a poly(1,4-phenylene sulfide), a polylimonene, a poly(vinylalcohol-co-ethylene), a poly[N,N'-(1,3-phenylene)isophthalamide], a poly(1,4-phenylene ether-ether-sulfone), a poly(ethyleneoxide), a poly[butylene terephthalate-co-poly(alkylene glycol) terephthalate], a poly(ethylene glycol) diacrylate, a poly(4-vinylpyridine), a poly(DL-lactide), a poly(3,3',4,4'-benzophenonetetracarboxylic dianhydride-co-4,4'-oxydianiline/1,3-phenylenediamine), an agarose, a polyvinylidene fluoride homopolymer, a styrene butadiene copolymer, a phenolic resin, a ketone resin, a 4,5-difluoro-2,2-bis(trifluoromethyl)-1,3-dioxane, a salt thereof, and combinations thereof. In some embodiments, a masking component is present in a concentration of about 1% to about 10%, about 1% to about 5%, or about 2% by weight of the patterning composition.

Other contemplated components of a patterning composition suitable for use with the disclosed methods include thiols, 1,9-Nonanedithiol solution, silane, silazanes, alkynes cystamine, N-Fmoc protected amino thiols, biomolecules, DNA, proteins, antibodies, collagen, peptides, biotin, and carbon nanotubes.

For a description of patterning compounds and patterning compositions, and their preparation and use, see Xia and Whitesides, Angew. Chem. Int. Ed., 37, 550-575 (1998) and references cited therein; Bishop et al., Curr. Opinion Colloid & Interface Sci., 1, 127-136 (1996); Calvert, J. Vac. Sci. Technol. B, 11, 2155-2163 (1993); Ulman, Chem. Rev., 96:1533 (1996) (alkanethiols on gold); Dubois et al., Annu. Rev. Phys. Chem., 43:437 (1992) (alkanethiols on gold); Ulman, An Introduction to Ultrathin Organic Films: From Langmuir-Blodgett to Self-Assembly (Academic, Boston, 1991) (alkanethiols on gold); Whitesides, Proceedings of the Robert A. Welch Foundation 39th Conference On Chemical Research Nanophase Chemistry, Houston, Tex., pages 109-121 (1995) (alkanethiols attached to gold); Mucic et al. Chem. Commun. 555-557 (1996) (describes a method of attaching 3' thiol DNA to gold surfaces); U.S. Pat. No. 5,472,881 (binding of oligonucleotide-phosphorothiolates to gold surfaces); Burwell, Chemical Technology, 4, 370-377 (1974) and Matteucci and Caruthers, J. Am. Chem. Soc., 103, 3185-3191 (1981) (binding of oligonucleotides-alkyl-siloxanes to silica and glass surfaces); Grabar et al., Anal. Chem., 67, 735-743 (binding of aminoalkylsiloxanes and for similar binding of mercaptoalkylsiloxanes); Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interfate Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langmuir, 3,951 (1987) (aromatic carboxylic acids, aldehydes, alcohols and methoxy groups on titanium dioxide and silica); and Lec et al., J. Phys. Chem., 92, 2597 (1988) (rigid phosphates on metals); Lo et al., J. Am. Chem. Soc., 118, 11295-11296 (1996) (attachment of pyrroles to superconductors); Chen et al., J. Am. Chem. Soc., 117, 6374-5 (1995) (attachment of amines and thiols to superconductors); Chen et al., Langmuir, 12, 2622-2624 (1996) (attachment of thiols to superconductors); McDevitt et al., U.S. Pat. No. 5,846,909 (attachment of amines and thiols to superconductors); Xu et al., Langmuir, 14, 6505-6511 (1998) (attachment of amines to superconductors); Mirkin et al., Adv. Mater. (Weinheim, Ger.), 9, 167-173 (1997) (attachment of amines to superconductors); Hovis et al., J. Phys. Chem. B, 102, 6873-6879 (1998) (attachment of olefins and dienes to silicon); Hovis et al., Surf. Sci., 402-404, 1-7 (1998) (attachment of olefins and dienes to silicon); Hovis et al., J. Phys. Chem. B, 101, 9581-9585 (1997) (attachment of olefins and dienes to silicon); Hamers et al., J. Phys. Chem. B, 101, 1489-1492 (1997) (attachment of olefins and dienes to silicon); Hamers et al., U.S. Pat. No. 5,908,692 (attachment of olefins and dienes to silicon); Ellison et al., J. Phys. Chem. B, 103, 6243-6251 (1999) (attachment of isothiocyanates to silicon); Ellison et al., J. Phys. Chem. B, 102, 8510-8518 (1998) (attachment of azoalkanes to silicon); Ohno et al., Mol. Cryst. Liq. Cryst. Sci. Technol., Sect. A, 295, 487-490 (1997) (attachment of thiols to GaAs); Reuter et al., Mater. Res. Soc. Symp. Proc., 380, 119-24 (1995) (attachment of thiols to GaAs); Bain, Adv. Mater. (Weinheim, Fed. Repub. Ger.), 4, 591-4 (1992) (attachment of thiols to GaAs); Sheen et al., J. Am. Chem. Soc., 114, 1514-15 (1992) (attachment of thiols to GaAs); Nakagawa et al., Jpn. J. Appl. Phys., Part 1, 30, 3759-62 (1991) (attachment of thiols to GaAs); Lunt et al., J. Appl. Phys., 70, 7449-67 (1991) (attachment of thiols to GaAs); Lunt et al., J. Vac. Sci. Technol., B, 9, 2333-6 (1991) (attachment ofthiols to GaAs); Yamamoto et al., Langmuir ACS ASAP, web release number la990467r (attachment of thiols to InP); Gu et al., J. Phys. Chem. B, 102, 9015-9028 (1998) (attachment of thiols to InP); Menzel et al., Adv. Mater. (Weinheim, Ger.), 11, 131-134 (1999) (attachment of disulfides to gold); Yonezawa et al., Chem. Mater., 11, 33-35 (1999) (attachment of disulfides to gold); Porter et al., Langmuir, 14, 7378-7386 (1998) (attachment of disulfides to gold); Son et al., J. Phys. Chem., 98, 8488-93 (1994) (attachment of nitriles to gold and silver); Steiner et al., Langmuir, 8, 2771-7 (1992) (attachment of nitriles to gold and copper); Solomun et al., J. Phys. Chem., 95, 10041-9 (1991) (attachment of nitriles to gold); Solomun et al., Ber. Bunsen-Ges. Phys. Chem., 95, 95-8 (1991) (attachment of nitriles to gold); Henderson et al., Inorg. Chim. Acta, 242, 115-24 (1996) (attachment of isonitriles to gold); Huc et al., J. Phys. Chem. B, 103, 10489-10495 (1999) (attachment of isonitriles to gold); Hickman et al., Langmuir, 8, 357-9 (1992) (attachment of isonitriles to platinum); Steiner et al., Langmuir, 8, 90-4 (1992) (attachment of amines and phospines to gold and attachment of amines to copper); Mayya et al., J. Phys. Chem. B, 101, 9790-9793 (1997) (attachment of amines to gold and silver); Chen et al., Langmuir, 15, 1075-1082 (1999) (attachment of carboxylates to gold); Tao, J. Am. Chem. Soc., 115, 4350-4358 (1993) (attachment of carboxylates to copper and silver); Laibinis et al., J. Am. Chem. Soc., 114, 1990-5 (1992) (attachment of thiols to silver and copper); Laibinis et al., Langmuir, 7, 3167-73 (1991) (attachment of thiols to silver); Fenter et al., Langmuir, 7, 2013-16 (1991) (attachment of thiols to silver); Chang et al., Am. Chem. Soc., 116, 6792-805 (1994) (attachment of thiols to silver); Li et al., J. Phys. Chem., 98, 11751-5 (1994) (attachment of thiols to silver); Li et al., Report, 24 pp (1994) (attachment of thiols to silver); Tarlov et al., U.S. Pat. No. 5,942,397 (attachment of thiols to silver and copper); Waldeck, et al., PCT application WO/99/48682 (attachment of thiols to silver and copper); Gui et al., Langmuir, 7, 955-63 (1991) (attachment of thiols to silver); Walczak et al., J. Am. Chem. Soc., 113, 2370-8 (1991) (attachment of thiols to silver); Sangiorgi et al., Gazz. Chim. Ital., 111, 99-102 (1981) (attachment of amines to copper); Magallon et al., Book of Abstracts, 215th ACS National Meeting, Dallas, Mar. 29-Apr. 2, 1998, COLL-048 (attachment of amines to copper); Patil et al., Langmuir, 14, 2707-2711 (1998) (attachment of amines to silver); Sastry et al., J. Phys. Chem. B, 101, 4954-4958 (1997) (attachment of amines to silver); Bansal et al., J. Phys. Chem. B. 102, 4058-4060 (1998) (attachment of alkyl lithium to silicon); Bansal et al., J. Phys. Chem. B, 102, 1067-1070 (1998) (attachment of alkyl lithium to silicon); Chidsey, Book of Abstracts, 214th ACS National Meeting, Las Vegas, Nev., Sep. 7-11, 1997, I&EC-027 (attachment of alkyl lithium to silicon); Song, J. H., Thesis, University of California at San Diego (1998) (attachment of alkyl lithium to silicon dioxide); Meyer et al., J. Am. Chem. Soc., 110, 4914-18 (1988) (attachment of amines to semiconductors); Brazdil et al. J. Phys. Chem., 85, 1005-14 (1981) (attachment of amines to semiconductors); James et al., Langmuir, 14, 741-744 (1998) (attachment of proteins and peptides to glass); Bernard et al., Langmuir, 14, 2225-2229 (1998) (attachment of proteins to glass, polystyrene, gold, silver and silicon wafers); Pereira et al., J. Mater. Chem., 10, 259 (2000) (attachment of silazanes to $SiO_2$); Pereira et al., J. Mater. Chem., 10, 259 (2000) (attachment of silazanes to $SiO_2$); Dammel, Diazonaphthoquinone Based Resists (1st ed., SPIE Optical Engineering Press, Bellingham, Wash., 1993) (attachment of silazanes to $SiO_2$); Anwander et al., J. Phys. Chem. B, 104, 3532 (2000) (attachment of silazanes to SiO$_2$); Slavov et al., J. Phys. Chem., 104, 983 (2000) (attachment of silazanes to SiO$_2$).

Surfaces to be Patterned

Surfaces suitable for use in methods disclosed herein include, but are not limited to, metals, alloys, composites, crystalline materials, amorphous materials, conductors, semiconductors, optics, fibers, inorganic materials, glasses, ceramics (e.g., metal oxides, metal nitrides, metal silicides, and combinations thereof), zeolites, polymers, plastics, organic materials, minerals, biomaterials, living tissue, bone, films thereof, thin films thereof, laminates thereof, foils thereof, composites thereof, and combinations thereof. A surface can comprise a semiconductor such as, but not limited to: crystalline silicon, polycrystalline silicon, amorphous silicon, p-doped silicon, n-doped silicon, silicon oxide, silicon germanium, germanium, gallium arsenide, gallium arsenide phosphide, indium tin oxide, and combinations thereof. A surface can comprise a glass such as, but not limited to, undoped silica glass (SiO$_2$), fluorinated silica glass, borosilicate glass, borophosphorosilicate glass, organosilicate glass, porous organosilicate glass, and combinations thereof. The surface can be a non-planar surface, such as pyrolytic carbon, reinforced carbon-carbon composite, a carbon phenolic resin, and the like, and combinations thereof. A surface can comprise a ceramic such as, but not limited to, silicon carbide, hydrogenated silicon carbide, silicon nitride, silicon carbonitride, silicon oxynitride, silicon oxycarbide, high-temperature reusable surface insulation, fibrous refractory composite insulation tiles, toughened unipiece fibrous insulation, low-temperature reusable surface insulation, advanced reusable surface insulation, and combinations thereof. A surface can comprise a flexible material, such as, but not limited to: a plastic, a metal, a composite thereof, a laminate thereof, a thin film thereof, a foil thereof, and combinations thereof.

Printing of Surface

The contacting time for the tips can be from about 0.001 s to about 60 s, depending upon the amount of patterning composition desired in any specific point on a surface. The contacting force can be controlled by altering the z-piezo of the piezo scanner or by other means that allow for controlled application of force across the tip array.

The surface can be contacted with a tip array a plurality of times, wherein the tip array, the surface or both move to allow for different portions of the surface to be contacted. The time and pressure of each contacting step can be the same or different, depending upon the desired pattern. The shape of the indicia or patterns has no practical limitation, and can include dots, lines (e.g., straight or curved, formed from individual dots or continuously), a preselected pattern, or any combination thereof.

The indicia resulting from the disclosed methods have a high degree of sameness, and thus are uniform or substantially uniform in size, and preferably also in shape. The individual indicia feature size (e.g., a dot or line width) is highly uniform, for example within a tolerance of about 5%, or about 1%, or about 0.5%. The tolerance can be about 0.9%, about 0.8%, about 0.7%, about 0.6%, about 0.4%, about 0.3%, about 0.2%, or about 0.1%. Non-uniformity of feature size and/or shape can lead to roughness of indicia that can be undesirable for sub-micron type patterning.

The feature size can be about 10 nm to about 1 mm, about 10 nm to about 500 µm, about 10 nm to about 100 µm, about 50 nm to about 100 µm, about 50 nm to about 50 µm, about 50 nm to about 10 µm, about 50 nm to about 5 µm, or about 50 nm to about 1 µm. Features sizes can be less than 1 µm, less than about 900 nm, less than about 800 nm, less than about 700 nm, less than about 600 nm, less than about 500 nm, less than about 400 nm, less than about 300 nm, less than about 200 nm, less than about 100 nm, or less than about 90 nm.

EXAMPLES

The following non-limiting examples demonstrate experiments that were conducted with a 384 spot array, where each spot is composed of approximately 400 nanoarrays, and where each array has a 10×10 arrangement of 750 nm features that present extracellular matrix (ECM) proteins surrounded by an immobilized phosphopeptide. Cells attached to the individual nanoarrays, where they were cultured and treated with small molecules—and where each of the 384 cultures was treated with a unique compound—after which the media was removed and the cells were lysed. Phosphatase enzymes in the proximal lysate then acted on the immobilized phosphopeptide substrate to convert it to the dephosphorylated form. After the lysate was removed, the array was analyzed by SAMDI mass spectrometry to identify the extent of dephosphorylation and therefore the amount of enzyme activity in the cell.

Reagents. All reagents were obtained from the supplier and used as received. Phosphatase inhibitor I was purchased from Santa Cruz Biotechnology. Hexadecylphosphonic acid and 2,4,6-trihodroxyacetophenone were purchased from Sigma Aldrich. Amino acids and peptide synthesis reagents were obtained from Anaspec. All peptides were synthesized following standard solid phase peptide synthesis protocols as previously described.[7,8,11] A buffer comprising 20 mM Tris at pH 8.0 containing 0.5% triton was used for lysis and a protease inhibitor tablet obtained from Roche (cOmplete, Mini EDTA-free) was added to the lysis buffer prior use.

Preparation of SAMs. Glass slides were first cleaned by sonicating in ethanol for 30 min and dried under a stream of N$_2$. An electron beam evaporator was used to first deposit 5 nm of Ti onto the glass slides and subsequently vented to oxidize the Ti layer. Next, an aluminum mask having holes in a 384-well format was placed on top of the glass slide and an additional 5 nm of Ti were deposited followed by 35 nm of Au. The pen array was then immersed in a solution of MHA (10 mM in ethanol) for 1 minute, dried with N$_2$, and mounted on a scanning probe instrument (Park Systems) where the humidity inside the chamber was fixed at 50%. A patterning routine was programmed in the instrument with tip-surface contact times of 1 s for 750 nm features. The Au-coated glass slides were soaked overnight at 4° C. in an ethanolic solution containing a 1:4 ratio of an asymmetric disulfide terminated with a maleimide group and a tri (ethylene glycol) group and a symmetric disulfide terminated with tri(ethylene glycol) groups, with a 0.5 mM total disulfide concentration. The functionalized glass slides were rinsed with ethanol and then immersed in a 10 mM ethanolic solution of hexadecyl phosphonic acid for 10 min. After rinsing with ethanol and drying under air, a solution (3 µL) consisting of 40 µM phosphatase peptide substrate in 1×PBS at pH 7.5 was delivered onto each spot and incubated in a humidity chamber for 1 h at 37° C. Surfaces were characterized by XPS using an electron spectroscopy for chemical analysis (ESCA) probe (Thermo Scientific ESCALAB 250 xi). Following peptide immobilization, the substrates were exposed to a solution of human plasma fibronectin (30 µg/mL in PBS) overnight at 4° C.

Cell-Based Assay for Enzyme Activity. HeLa cells were obtained from ATCC and cultured in DMEM medium supplemented with fetal bovine serum, glutamine, penicillin and streptomycin. All cells were cultured in a humidified incubator at 37° C. and 5% $CO_2$. Cells were trypsinized and suspended in media, and the average number of cells per µL was estimated using a hemocytometer to seed the desired number of cells per spot. The volume of media per spot was 3 µL for all experiments. Cells were cultured on the monolayers presenting fibronectin and the phosphatase peptide substrate on glass slides for 2 hours under standard growth conditions. Lysis buffer (1 µL) was delivered manually to each spot and the lysate was allowed to react with the monolayer for 1 hour at 37° C. in a humidity chamber. The surfaces were then rinsed with DI water and ethanol, and dried with air. A solution of 2,4,6-trihydroxyacetopehenone (THAP) in acetone (30 mg/mL) was delivered to each spot on the array and the surfaces were analyzed using an Applied Biosystems 5800 MALDI TOF/TOF instrument with a 20 kV accelerating voltage in positive reflector mode.

Lysis Promotes Interaction of PTPs with Peptide Substrate. A mild cell detachment reagent (TrypLE) was introduced to remove cells following culture on the patterned surfaces. This reagent (3 µL) was delivered to each spot and incubated for 5 minutes. The solution was then removed and the glass slide was rinsed with PBS, followed by DI water and dried with $N_2$. A matrix solution was applied prior to mass spectrometric analysis as described above.

Evaluation of PTP Inhibition with SAMDI. HeLa cells were seeded at 500 cells per spot on monolayers presenting phosphatase peptide substrates and fibronectin features. Following cell attachment and culture for 2 hours, PTPI-I (1 µL solution in media) was delivered to each spot to achieve a final concentration of 300 µM in media and incubated for 2 hours. Following removal of the media, the lysis buffer with protease inhibitor was applied to each spot and incubated for 1 hour at 37° C. in a humidified chamber. The slide was then rinsed with water, ethanol and dried. Matrix was applied prior to analysis by mass spectrometry.

Figure 2:
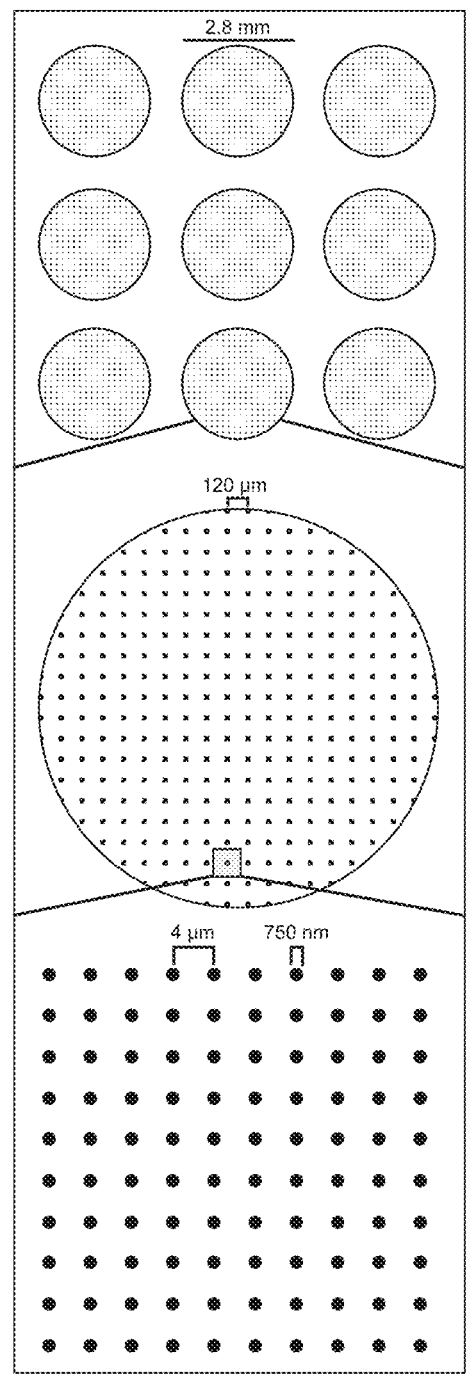
FIG. 2 shows pattern arrangement across multiple length scales. Nanoarrays were prepared on 384-well format gold islands, where each island was patterned using PPL to yield ~428 arrays of MHA features. Each array was patterned over a 40×40 μm$^2$ area having a total of 100 MHA features arranged in a 10×10 square matrix. The size of each individual MHA feature corresponds to ~750 nm.
Figure 10:
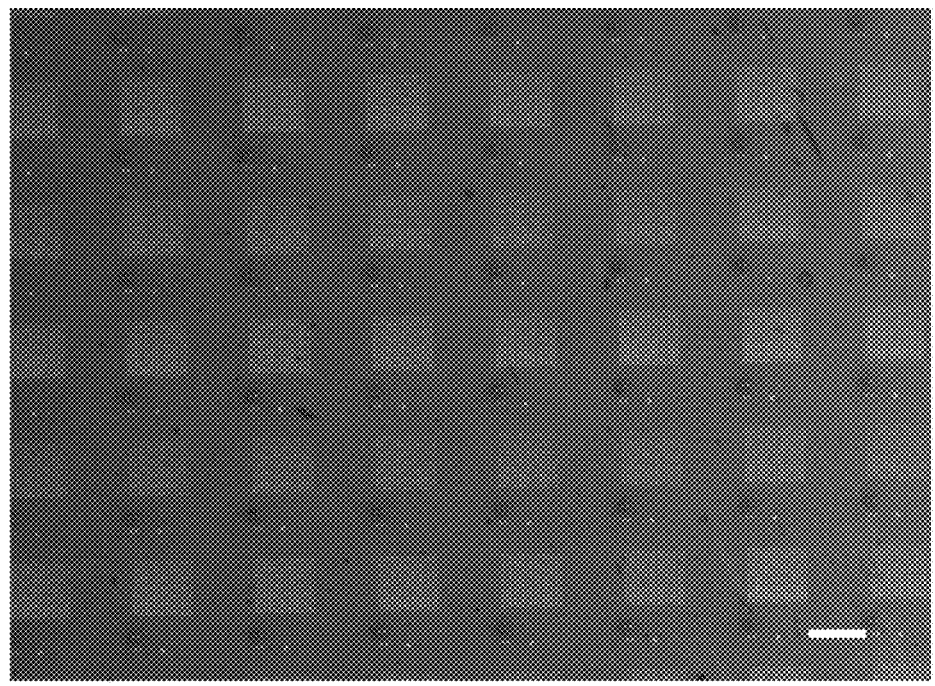
FIG. 10 shows MHA features arranged in a square array patterned by polymer pen lithography (PPL). Optical micrograph of raised gold features ~1 μm in diameter made by chemical etching (with an aqueous solution of 13.3 mM Fe(NO3)3 and 20 mM thiourea) a portion of a glass slide having PPL-patterned mercaptohexadecanoic acid (MHA) features. The scale bar is 60 μm.

To prepare the array plates, titanium was first evaporated onto a glass slide and then gold was deposited through a mask having an array of holes arranged in the standard 384-well format.[15] The slide was then immersed in a solution of hexadecylphosphonic acid (10 mM in ethanol) for 10 minutes to form a hydrophobic monolayer on the titanium dioxide areas surrounding the gold circular regions. This monolayer serves to confine aqueous solutions to the circular regions of gold and to isolate each reaction. Next, PPL was used to create patterns of a mercaptohexadecanoic acid (MHA) monolayer on the gold-coated regions of the glass plate. This technique has proven useful for patterning proteins, peptides, oligonucleotides, and small molecules for a wide variety of biological applications.[16-21] In PPL, an elastomeric pen array is coated with a molecular 'ink' and subsequently mounted to a scanning probe instrument and pressed onto a gold-coated slide, to create an array of circular MHA monolayer features. This step can be repeated with translational movement of the array to create arbitrary patterns.[7,11] The feature size can be easily controlled and customized by adjusting the amount of force applied to the pen array and the time the pen array remains in contact with the surface.[9] Here, a SAMDI array that has a portion of a microtiter plate with 384 gold islands was used, wherein each island is 2.8 mm in diameter.[22] PPL was then used to pattern MHA features within each island. In a typical experiment, a poly(dimethylsiloxane) (PDMS) pen array (1.2×1.2 cm$^2$) having 10,000 pens, corresponding to a pen-to-pen distance of 120 µm and each coated with a solution of MHA (10 mM in ethanol), was used to generate 428 regions containing 10×10 square arrays of MHA features, each measuring 750 nm in diameter and spaced by a center-to-center distance of 4.4 µm within each gold island (FIG. 2). These MHA features, when later modified with the appropriate ECM protein, mediate the attachment of an individual HeLa cell to each square array.[23] The patterning step was verified by chemically etching a portion of the surface with a mixed aqueous solution of iron nitrate (13.3 mM) and thiourea (20 mM) to remove the non-patterned gold film (FIG. 10). The non-patterned areas were subsequently functionalized with a mixed monolayer that presents maleimide groups at a density of 10% against a background of tri(ethylene glycol) groups.

Figure 3A:
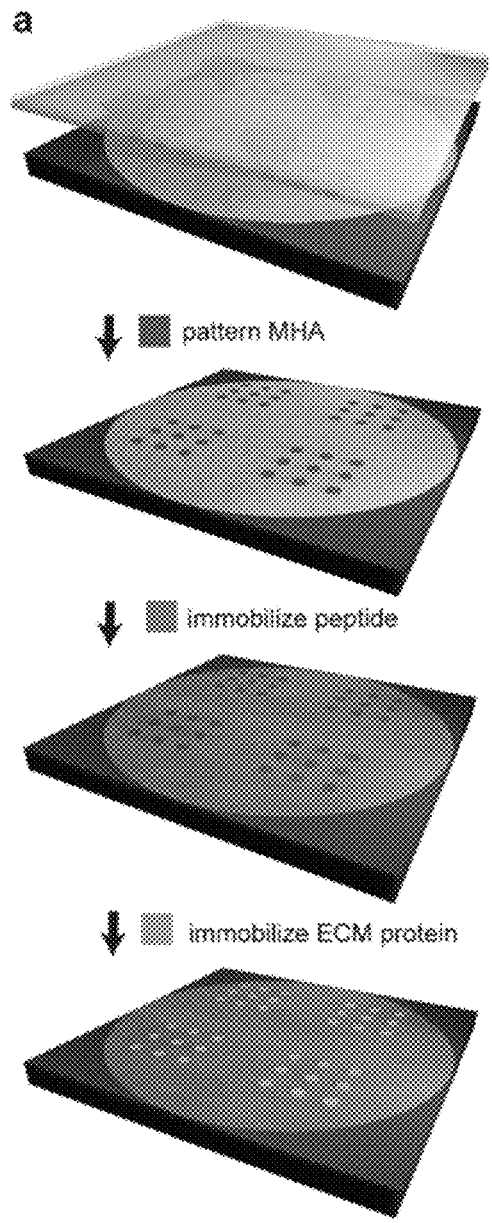
FIGS. 3A-3D shows nanoarrays were prepared by using PPL to pattern mercaptohexadecanoic acid (MHA) on a gold coated surface in many 10×10 arrays where each spot was 750 nm in diameter and where neighboring spots had a center-to-center spacing of 4.4 μm (a). The remaining areas of gold were then modified with a monolayer presenting maleimide groups against a background of tri(ethylene glycol) groups and used to immobilize a cysteine terminated phosphopeptide (as in b). The surface was then treated with a solution of fibronectin to allow adsorption of the extracellular matrix protein to the MHA nanoarray. A SAMDI spectrum of the monolayer confirms immobilization of the peptide (c). The fluorescence micrograph shows fibronectin patterned nanorrays stained with mouse anti-fibronectin antibody and AlexaFluor568-conjugated goat anti-mouse IgG (d). The scale bar is 40 μm.
Figure 3B:
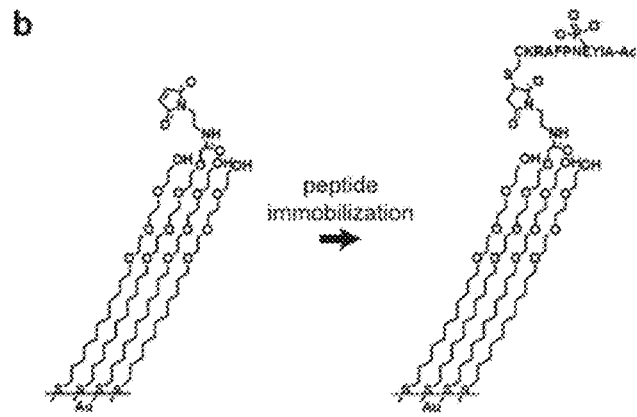
Figure 3C:
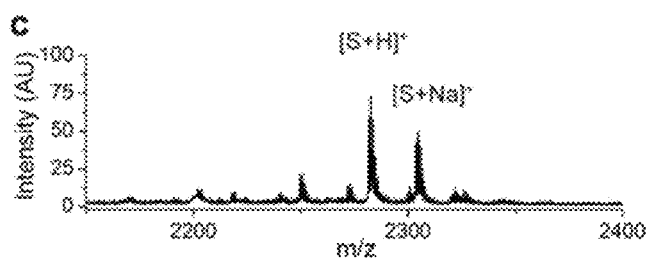
Figure 3D:
Figure 11:
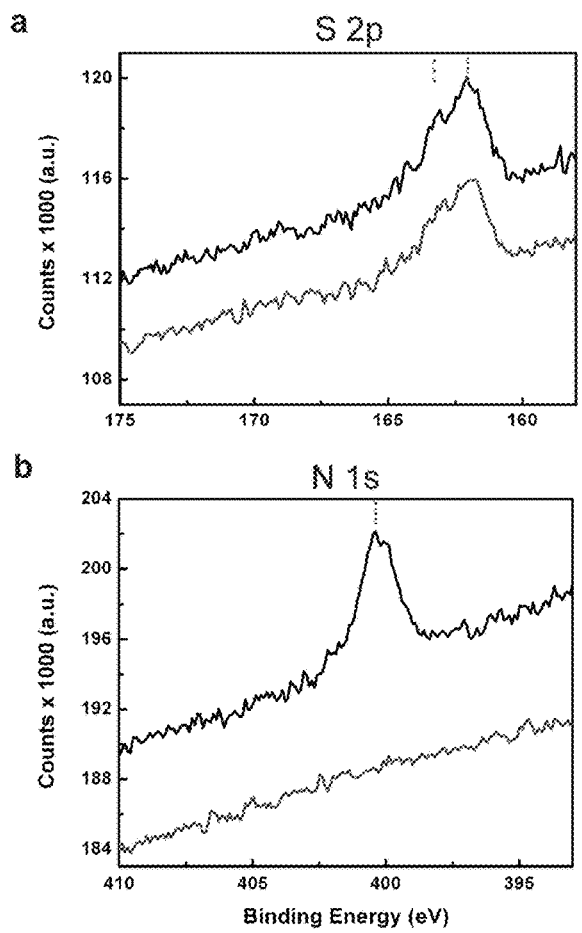
FIG. 11 shows XPS spectra collected after peptide immobilization on Au regions that present a maleimide-terminated monolayer along with MHA nanoarrays. The presence of sulfur (a) and nitrogen (b) peaks indicate the availability of amide bonds and thiols on the surface (black trace), while a control surface consisting of a uniform MHA monolayer (blue trace) only shows presence of thiols. Dashed lines denote the N (1s) and S (2p) peak positions.

Finally, a peptide substrate for phosphotyrosine enzymes (AIpYENPFARKC (SEQ ID NO: 2), where p denotes phosphorylation of the tyrosine residue)[24-26] was covalently immobilized by a conjugate addition of the terminal cysteine residue to the maleimide groups present on the monolayer.[27] SAMDI mass spectra confirmed that peptide immobilization was complete, and X-ray photoelectron spectroscopy (XPS) characterization showed the presence of sulfur and nitrogen peaks in the resulting monolayer consistent with the presence of thiols and amide bonds, respectively (FIG. 3C and FIG. 11). Finally, the patterned surfaces were immersed in a solution of fibronectin (30 µg/mL in PBS) to allow the non-specific adsorption of protein to the patterned MHA features. Immunofluorescent labeling of fibronectin confirmed the adsorption only to the regions of MHA (FIG. 3D). As disclosed herein, this approach is applicable to other ECM attachment proteins, such as, without limitation, collagen and laminin, which can also adsorb to self-assembled monolayers by way of non-specific interactions.

Figure 4A:
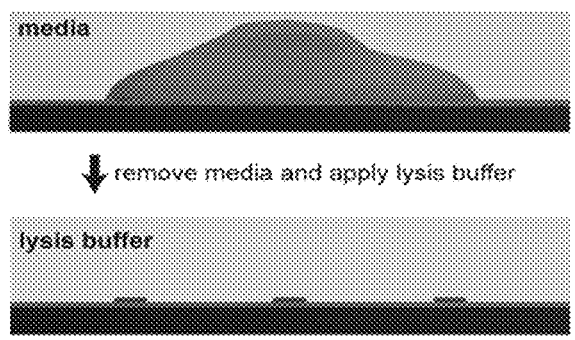
FIGS. 4A-4C show cell culture and lysis on mixed monolayers. Cells were cultured on patterned monolayers. Individual cells attached to each 10×10 fibronectin nanoarray and remained confined to these regions of the surface (b). The media was then removed from the entire plate and a lysis buffer was added to each spot of the 384 spot array to allow phosphatase enzymes in the lysate to act on peptides immobilized on the monolayer. The scale bar is 500 μm. SAMDI spectra of the surface after removal of the lysate showed a peak corresponding to generation of the dephosphorylated product (c, top). Addition of the phosphatase inhibitor PTPI-I to the lysis buffer resulted in a loss of phosphatase activity (middle) as did proteolytic removal of the cells without lysis (bottom).
Figure 4B:
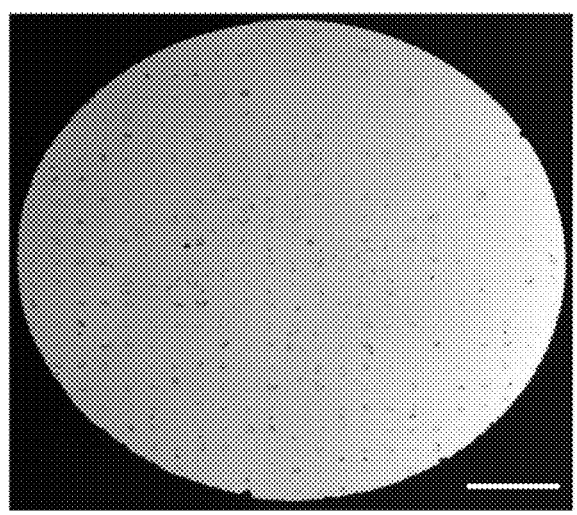
Figure 4C:
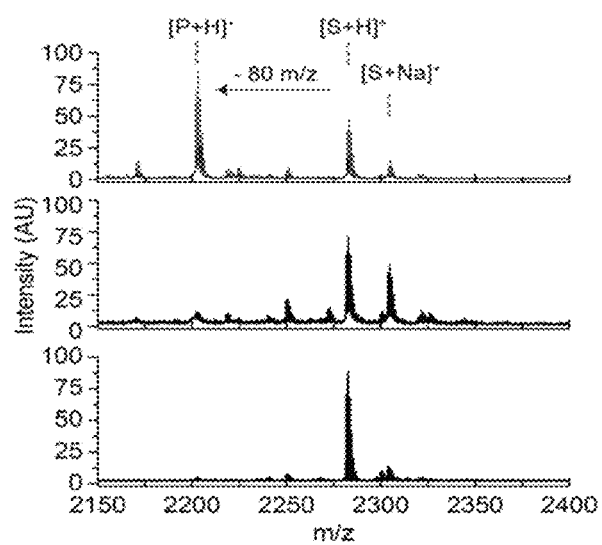

HeLa cells were seeded on the fibronectin nanopatterned surfaces and cultured the cells for two hours under standard media conditions (FIG. 4A). The cells spread fully within the 10×10 nanoarrays of fibronectin, and they remained adherent during the culture (FIGS. 4B and 4C). Cells were only observed on the patterned regions presenting the fibronectin, and cells remained confined to those regions of the surface, showing that the tri(ethylene glycol)-terminated monolayers were effective at preventing cell adhesion and spreading beyond the patterned matrix. After two hours in culture, the monolayers were rinsed with PBS to remove the media and then a lysis buffer containing a protease inhibitor cocktail was applied to each patterned region. The solutions were kept at 37° C. for one hour to allow enzymes in the lysate to interact with the phosphopeptides on the monolayer. The mixed monolayer was rinsed with PBS buffer and then treated with 2,4,6-trihydroxyacetophenone (THAP) matrix (30 mg/mL in acetone) and analyzed with SAMDI-MS.

A control array that was not seeded with cells was first analyzed and peaks were observed in the SAMDI spectrum that corresponded to asymmetric disulfides terminated in one phosphopeptide and one tri(ethylene glycol) group (m/z=2282) as well as the Na$^+$ (m/z=2304) and K$^+$ (m/z=2320) adducts of this molecule (FIG. 3C). For arrays that were treated with cells that had been lysed, the SAMDI spectra revealed corresponding peaks appearing at 80 Da lower mass, which is consistent with dephosphorylation of the peptide (FIG. 4C). The spectra were similar to those acquired from a monolayer that only presented the phosphopeptide against the tri(ethylene glycol) background and that was treated with a lysate isolated in the conventional manner. Hence, the nanopatterned fibronectin features did not interfere with the enzyme action on the peptide or with the SAMDI mass spectrometry of the intervening monolayer. This was expected, since the fibronectin was present on approximately 1% of the patterned surface, leaving most of the monolayer available for analysis by SAMDI, and also because the protein would be observed at a much higher mass range in the spectrum.

It was confirmed that the phosphatase activity that was observed was due to enzymes present in the cell lysate. For example, when cells were cultured for two hours, and then removed by treatment with the protease TrypLE, a selective protease that reduces the digestion of cell surface proteins, the resulting surfaces had essentially no dephosphorylated peptide, showing that potential secretion of phosphatases by the cell did not significantly contribute to the measurements (FIG. 4C). Similarly, conditioned media obtained from cell cultures was assayed and phosphatase activity was not observed. A known phosphotyrosine phosphatase inhibitor was also introduced during cell culture to confirm that the activity was due to cellular phosphatases. PTP Inhibitor I (PTPI-I), a covalent inhibitor,[28] was added to cell cultures (300 µM) during the two hour culture period. Following lysis and analysis as described above, a 92% decrease in phosphatase activity was observed (FIG. 4C). Together, these experiments demonstrated that the TCAL assay measures enzyme activities present in the cell lysate.

The nanopatterned surfaces reported herein are significant because they expand the use of the TCAL assay to a broad range of cell types.[14] Monolayers that are patterned with nanoarrays of ECM proteins can support the adhesion and culture of cells and still be analyzed with SAMDI mass spectrometry. Hence, established cultures that use glass or plastic surfaces that are uniformly modified with a layer of ECM can be readily translated to the TCAL assay with these nanopatterned surfaces. This approach is also significant because it can measure activities in lysates prepared from as few as ten cells and because there is no processing or delay between generation and assay of the lysate, which often leads to loss of protein activity.[14] The use of SAMDI-MS provides a label-free assay of a broad range of enzyme activities, making this format quite general for applications in different drug development targets.[30,31] The tri(ethylene glycol)-terminated monolayers have been shown to remain inert for up to one week in culture, making this approach compatible with most cell-based assay protocols.[32] Finally, the TCAL-SAMDI method is not limited to the use of peptides as substrates for the relevant enzyme, but can also use carbohydrates,[33] small molecules and protein substrates,[34] since each of these molecules can be immobilized to a monolayer and characterized with SAMDI mass spectrometry.

Traditionally, cell-based assays have been employed when the phenotype of interest could not be translated to an enzyme activity—for example, a validated target for blocking metastasis is still lacking. They have not been used when a validated target is available, because molecular assays are faster, less expensive, and far less limited as to the molecular activities that can be assayed. The strategy disclosed herein narrows this gap between cell-based and molecular assays and promises to increase the use of cell-based assays in the first phase of drug discovery programs. The ability to assay compounds in cells—which reveals aspects of entry, trafficking and effects owing to interaction with other cellular proteins—but with a molecular readout combines the advantages of molecular and cellular assays and represents a significant advance in both drug discovery and for fundamental studies of signal transduction.

DOCUMENTS REFERENCED IN THE DISCLOSURE

1. Inglese, J.; Johnson, R. L.; Simeonov, A.; Xia, M. H.; Zheng, W.; Austin, C. P.; Auld, D. S. *Nat. Chem. Biol.* 2007, 3, (8), 466-479.
2. Mahmoud, L.; Al-Saif, M.; Amer, H. M.; Sheikh, M.; Almajhdi, F. N.; Khabar, K. S. A. *J. Virol.* 2011, 85, (18), 9268-9275.
3. Meli, L.; Barbosa, H. S.; Hickey, A. M.; Gasimli, L.; Nierode, G.; Diogo, M. M.; Linhardt, R. J.; Cabral, J. M.; Dordick, J. S. *Stem Cell Res.* 2014, 13, (1), 36-47.
4. Kepp, O.; Galluzzi, L.; Lipinski, M.; Yuan, J.; Kroemer, G. *Nat. Rev. Drug Discov.* 2011, 10, (3), 221-37.
5. Liang, C. C.; Park, A. Y.; Guan, J. L. *Nat. Protoc.* 2007, 2, (2), 329-33.
6. Tsien, R. Y. *Annu. Rev. Biochem.* 1998, 67, 509-544.
7. Huo, F.; Zheng, Z.; Zheng, G.; Giam, L. R.; Zhang, H.; Mirkin, C. A. *Science* 2008, 321, (5896), 1658-60.
8. Braunschweig, A. B.; Huo, F.; Mirkin, C. A. *Nat. Chem.* 2009, 1, (5), 353-8.
9. Liao, X.; Braunschweig, A. B.; Zheng, Z.; Mirkin, C. A. *Small* 2010, 6, (10), 1082-6.
10. Giam, L. R.; Mirkin, C. A. *Angew. Chem., Int. Ed.* 2011, 50, (33), 7482-5.
11. Eichelsdoerfer, D. J.; Liao, X.; Cabezas, M. D.; Morris, W.; Radha, B.; Brown, K. A.; Giam, L. R.; Braunschweig, A. B.; Mirkin, C. A. *Nat. Protoc.* 2013, 8, (12), 2548-60.
12. Mrksich, M. *ACS Nano* 2008, 2, (1), 7-18.
13. Frantz, C.; Stewart, K. M.; Weaver, V. M. *J. Cell Sci.* 2010, 123, (Pt 24), 4195-200.
14. Berns, E. J.; Cabezas, M. D.; Mrksich, M. *Small* 2016, 12, (28), 3811-8.
15. Gurard-Levin, Z. A.; Scholle, M. D.; Eisenberg, A. H.; Mrksich, M. *ACS Comb. Sci.* 2011, 13, (4), 347-50.
16. Piner, R. D.; Zhu, J.; Xu, F.; Hong, S.; Mirkin, C. A. *Science* 1999, 283, (5402), 661-3.
17. Lee, K. B.; Lim, J. H.; Mirkin, C. A. *J. Am. Chem. Soc.* 2003, 125, (19), 5588-9.
18. Lim, J. H.; Ginger, D. S.; Lee, K. B.; Heo, J.; Nam, J. M.; Mirkin, C. A. *Angew. Chem., Int. Ed.* 2003, 42, (20), 2309-12.
19. Ginger, D. S.; Zhang, H.; Mirkin, C. A. *Angew. Chem., Int. Ed.* 2004, 43, (1), 30-45.
20. Salaita, K.; Wang, Y.; Mirkin, C. A. *Nat. Nanotechnol.* 2007, 2, (3), 145-55.
21. Vega, R. A.; Shen, C. K.; Maspoch, D.; Robach, J. G.; Lamb, R. A.; Mirkin, C. A. *Small* 2007, 3, (9), 1482-5.
22. Gurard-Levin, Z. A.; Mrksich, M. *Annu. Rev. Anal. Chem.* 2008, 1, 767-800.
23. Giam, L. R.; Massich, M. D.; Hao, L.; Shin Wong, L.; Mader, C. C.; Mirkin, C. A. *Proc. Natl. Acad. Sci. U.S.A.* 2012, 109, (12), 4377-82.
24. Songyang, Z.; Shoelson, S. E.; Chaudhuri, M.; Gish, G.; Pawson, T.; Haser, W. G.; King, F.; Roberts, T.; Ratnofsky, S.; Lechleider, R. J.; et al. *Cell* 1993, 72, (5), 767-78.
25. Songyang, Z.; Carraway, K. L.; Eck, M. J.; Harrison, S. C.; Feldman, R. A.; Mohammadi, M.; Schlessinger, J.; Hubbard, S. R.; Smith, D. P.; Eng, C.; Lorenzo, M. J.; Ponder, B. A. J.; Mayer, B. J.; Cantley, L. C. *Nature* 1995, 373, (6514), 536-539.
26. Li, S.; Liao, X.; Mrksich, M. *Langmuir* 2013, 29, (1), 294-8.
27. Houseman, B. T.; Gawalt, E. S.; Mrksich, M. *Langmuir* 2003, 19, (5), 1522-1531.
28. Arabaci, G.; Guo, X. C.; Beebe, K. D.; Coggeshall, K. M.; Pei, D. *J. Am. Chem. Soc.* 1999, 121, (21), 5085-5086.

29. Ruoslahti, E. *Annu. Rev. Cell Dev. Biol.* 1996, 12, 697-715.
30. Cabrera-Pardo, J. R.; Chai, D. I.; Liu, S.; Mrksich, M.; Kozmin, S. A. *Nat. Chem.* 2013, 5, (5), 423-7.
31. Patel, K.; Sherrill, J.; Mrksich, M.; Scholle, M. D. *J. Biomol. Screen* 2015, 20, (7), 842-8.
32. Mrksich, M. *Acta Biomater.* 2009, 5, (3), 832-41.
33. Ban, L.; Pettit, N.; Li, L.; Stuparu, A. D.; Cai, L.; Chen, W.; Guan, W.; Han, W.; Wang, P. G.; Mrksich, M. *Nat. Chem. Biol.* 2012, 8, (9), 769-73.
34. Feng, Y.; Mrksich, M. *Biochemistry* 2004, 43, (50), 15811-21.

What is claimed is:

1. A method of assaying activity of an intracellular enzyme, comprising:
   (a) printing a surface with an array of immobilized cell adhesion ligands and immobilized substrates for the intracellular enzyme by
      (i) coating a polymer pen lithography (PPL) tip array with a first monolayer reagent and printing the first monolayer reagent at selected positions on the surface to form an array of printed first monolayer reagent,
      (ii) incubating the array of printed first monolayer reagent with a second monolayer reagent such that the second monolayer reagent is adsorbed onto unprinted portions of the surface,
   wherein one of the first monolayer reagent and the second monolayer reagent comprises a monolayer reagent for adsorption of the cell adhesion ligand and the other comprises a monolayer reagent for chemical immobilization of the substrate for the intracellular enzyme,
      (iii) contacting the resulting array of step (ii) with the substrate for the intracellular enzyme under conditions to immobilize the substrate to the surface at the portion of the surface comprising the monolayer reagent for chemical immobilization,
      (iv) contacting the resulting array of step (ii) with the cell adhesion ligand under conditions to immobilize the cell adhesion ligand to the surface at the portion of the surface comprising the monolayer reagent for adsorption of the cell adhesion ligand;
   wherein steps (iii) and (iv) can be performed in either order;
   (b) contacting a cell and the surface of step (a), the contacting resulting in immobilization of the cell via interaction between the cell and the immobilized cell adhesion ligand;
   (c) contacting the immobilized cell with a lysing solution to form a cell lysate and release the enzyme, thereby allowing contact between the enzyme and the immobilized substrate to transform the immobilized substrate to a product, the product having a different mass than the substrate; and
   (d) measuring the amount of the product formed using matrix-assisted laser desorption/ionization mass spectrometry (MALDI-MS) to assay the activity of the enzyme.

2. The method of claim 1, wherein the surface comprises gold, silver, or copper.

3. The method of claim 1, wherein the monolayer reagent for adsorption of the cell adhesion ligand comprises mercaptohexadecanoic acid (MHA), hexadecane thiol, or a $C_{8-20}$ hydroxyalkane.

4. The method of claim 1, wherein the monolayer reagent for chemical immobilization of the substrate comprises an immobilizing moiety and an inert moiety.

5. The method of claim 4, wherein the immobilizing moiety comprises a maleimide, a thiol, an alkyne, an azide, an amine, or a carboxyl group.

6. The method of claim 4, wherein the inert moiety comprises mannitol or 3 to 6 ethylene glycol units.

7. The method of claim 1, wherein (i) one of the monolayer reagent for chemical immobilization of the substrate and the substrate comprises a maleimide and the other an alkane thiol; (ii) one of the monolayer reagent for chemical immobilization of the substrate and the substrate comprises an alkyne and the other an azide; or (iii) one of the monolayer reagent for chemical immobilization of the substrate and the substrate comprises an amine and the other a carboxyl group, so as to form a chemical bond between the monolayer reagent for chemical immobilization and the substrate.

8. The method of claim 1, wherein at least one of the immobilized substrate and the cell adhesion ligand comprises a peptide.

9. The method of claim 1, wherein the cell adhesion ligand comprises a RGD peptide or an extracellular matrix (ECM) protein.

10. The method of claim 1, wherein at least one of the cell adhesion ligand and the immobilized substrate is bound to the surface via a linker having a structure of formula I:

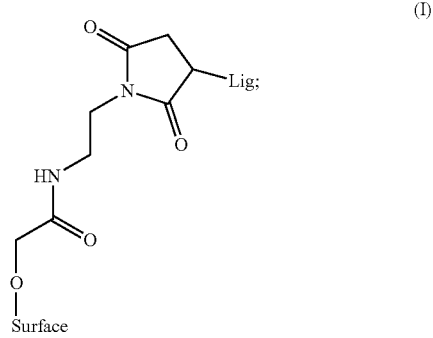

and Lig comprises the cell adhesion ligand or the immobilized substrate.

11. The method of claim 1, wherein the enzyme is a deacetylase, acetyltransferase, esterase, phosphorylase/kinase, phosphatase, protease, methylase, demethylase, or a DNA or RNA modifying enzyme.

12. The method of claim 11, wherein the immobilized substrate comprises an acylated peptide and the product comprises a deacylated peptide, or wherein the immobilized substrate comprises a deacylated peptide and the product comprises an acylated peptide.

13. The method of claim 11, wherein the immobilized substrate comprises a phosphorylated peptide and the product comprises a dephosphorylated peptide, or wherein the immobilized substrate comprises a dephosphorylated peptide and the product comprises a phosphorylated peptide.

14. The method of claim 11, wherein the immobilized substrate comprises a methylated peptide and the product comprises a demethylated peptide or wherein the immobilized substrate comprises a demethylated peptide and the product comprises a methylated peptide.

15. The method of claim 1, further comprising washing the surface after immobilizing the cell on the surface and before lysing the cell to remove all cells not immobilized onto the surface.

16. The method of claim 1, wherein the surface comprises a second immobilized substrate that associates with a second enzyme in the cell lysate to form a second product, the second product having a different mass than the second substrate.

17. The method of claim 1, wherein the lysate further comprises a potential modulator of binding of the enzyme and the immobilized substrate; and the activity of the enzyme assayed indicates the potential modulator's effect on the binding of the enzyme and the immobilized substrate in the presence of the potential modulator.

18. The method of claim 17, wherein the lysate comprises a second potential modulator of binding of the second enzyme and the second immobilized substrate; and the activity of the second enzyme assayed indicates the second potential modulator's effect on the binding of the second enzyme and the second immobilized substrate in the presence of the second potential modulator.

19. The method of claim 18, wherein the potential modulator or the second potential modulator is an inhibitor of the enzyme and immobilized substrate binding, or wherein the potential modulator or the second potential modulator is an activator of the enzyme and immobilized substrate binding.

20. The method of claim 1, wherein the PPL tip array comprises a compressible elastomeric polymer comprising a plurality of non-cantilevered tips each having a radius of curvature of less than 1 μm and a common substrate comprising a compressible elastomeric polymer, the tip array and the common substrate mounted onto a rigid support and the tip array, common substrate, and rigid support together being at least translucent.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Arg Thr Tyr
1

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Phosphorylation

<400> SEQUENCE: 2

Ala Ile Tyr Glu Asn Pro Phe Ala Arg Lys Cys
1               5                   10
```